US011471850B2

(12) United States Patent
Hourtane et al.

(10) Patent No.: US 11,471,850 B2
(45) Date of Patent: Oct. 18, 2022

(54) MICROFLUIDIC CASSETTE FOR SYNTHESIZING A RADIO-TRACER AND METHOD OF SYNTHESIZING A RADIO-TRACER WITH SUCH A CASSETTE

(71) Applicant: P M B, Peynier (FR)

(72) Inventors: Virginie Hourtane, Aix en Provence (FR); Laurent Tanguy, Aix en Provence (FR); Florian Pineda, Aix en Provence (FR)

(73) Assignee: P M B, Paynier (FR)

( * ) Notice: Subject to any disclaimer, the term of this patent is extended or adjusted under 35 U.S.C. 154(b) by 287 days.

(21) Appl. No.: 16/756,808

(22) PCT Filed: Oct. 12, 2018

(86) PCT No.: PCT/FR2018/052540
§ 371 (c)(1),
(2) Date: Apr. 16, 2020

(87) PCT Pub. No.: WO2019/077238
PCT Pub. Date: Apr. 25, 2019

(65) Prior Publication Data
US 2020/0238249 A1 Jul. 30, 2020

(30) Foreign Application Priority Data

Oct. 18, 2017 (FR) ..................... 1759802

(51) Int. Cl.
*B01J 19/00* (2006.01)
*A61K 51/08* (2006.01)
*C07B 59/00* (2006.01)

(52) U.S. Cl.
CPC ......... *B01J 19/0093* (2013.01); *A61K 51/083* (2013.01); *C07B 59/00* (2013.01);
(Continued)

(58) Field of Classification Search
CPC ........ A61K 51/00; A61K 51/02; A61K 51/04; A61K 51/08; A61K 51/083; B01J 19/00;
(Continued)

(56) References Cited

U.S. PATENT DOCUMENTS 8,206,593 B2 * 6/2012 Lee .................. B01F 33/30
210/640
8,377,398 B2 * 2/2013 McDevitt ........... G01N 21/6428
422/534
(Continued)

FOREIGN PATENT DOCUMENTS

| CN | 102233241 A | 11/2011 |
|---|---|---|
| CN | 106061608 A | 10/2016 |

(Continued)

OTHER PUBLICATIONS

International Search Report, PCT/FR2018/052540, dated Jan. 25, 2019.

(Continued)

*Primary Examiner* — Natasha E Young
(74) *Attorney, Agent, or Firm* — Nixon & Vanderhye

(57) ABSTRACT

The present application concerns a microfluidic cassette for synthesizing a radiotracer including a microfluidic circuit in a support card that includes at least one intake for supply by a vial, at least one isotope port, at least one reaction chamber, at least one mixing chamber, at least one formulation chamber, and at least one connection for a syringe, linked together by capillaries. Also disclosed is a method for synthesizing a radiotracer in such a cassette.

20 Claims, 22 Drawing Sheets

(52) U.S. Cl.
CPC .......... *B01J 2219/00783* (2013.01); *B01J 2219/00792* (2013.01); *B01J 2219/00813* (2013.01); *B01J 2219/00849* (2013.01); *B01J 2219/00876* (2013.01); *B01J 2219/00889* (2013.01); *C07B 2200/05* (2013.01)

(58) Field of Classification Search
CPC .......... B01J 19/0093; B01J 2219/00; B01J 2219/00274; B01J 2219/00277; B01J 2219/00351; B01J 2219/00389; B01J 2219/004; B01J 2219/00781; B01J 2219/00783; B01J 2219/00788; B01J 2219/00792; B01J 2219/00801; B01J 2219/0081; B01J 2219/00813; B01J 2219/00819; B01J 2219/00849; B01J 2219/00851; B01J 2219/00855; B01J 2219/00871; B01J 2219/00873; B01J 2219/00876; B01J 2219/0088; C07B 59/00; C07B 2200/00; C07B 2200/05
See application file for complete search history.

(56) References Cited

U.S. PATENT DOCUMENTS

| | | |
|---|---|---|
| 2005/0009101 A1 | 1/2005 | Blackburn |
| 2005/0170362 A1 | 8/2005 | Wada et al. |
| 2011/0150714 A1 | 6/2011 | Elizarov et al. |
| 2015/0157743 A1 | 6/2015 | McFarland et al. |
| 2016/0263545 A1* | 9/2016 | Eshima ............ B65B 3/003 |

FOREIGN PATENT DOCUMENTS

| | | |
|---|---|---|
| WO | WO 2011/037615 | 3/2011 |
| WO | WO 2013/101568 | 7/2013 |
| WO | WO 2015/101539 | 7/2015 |
| WO | WO 2016/166486 | 10/2016 |

OTHER PUBLICATIONS

Office Action issued in Chinese Patent Application No. 201880067746.0 dated May 10, 2021.

* cited by examiner

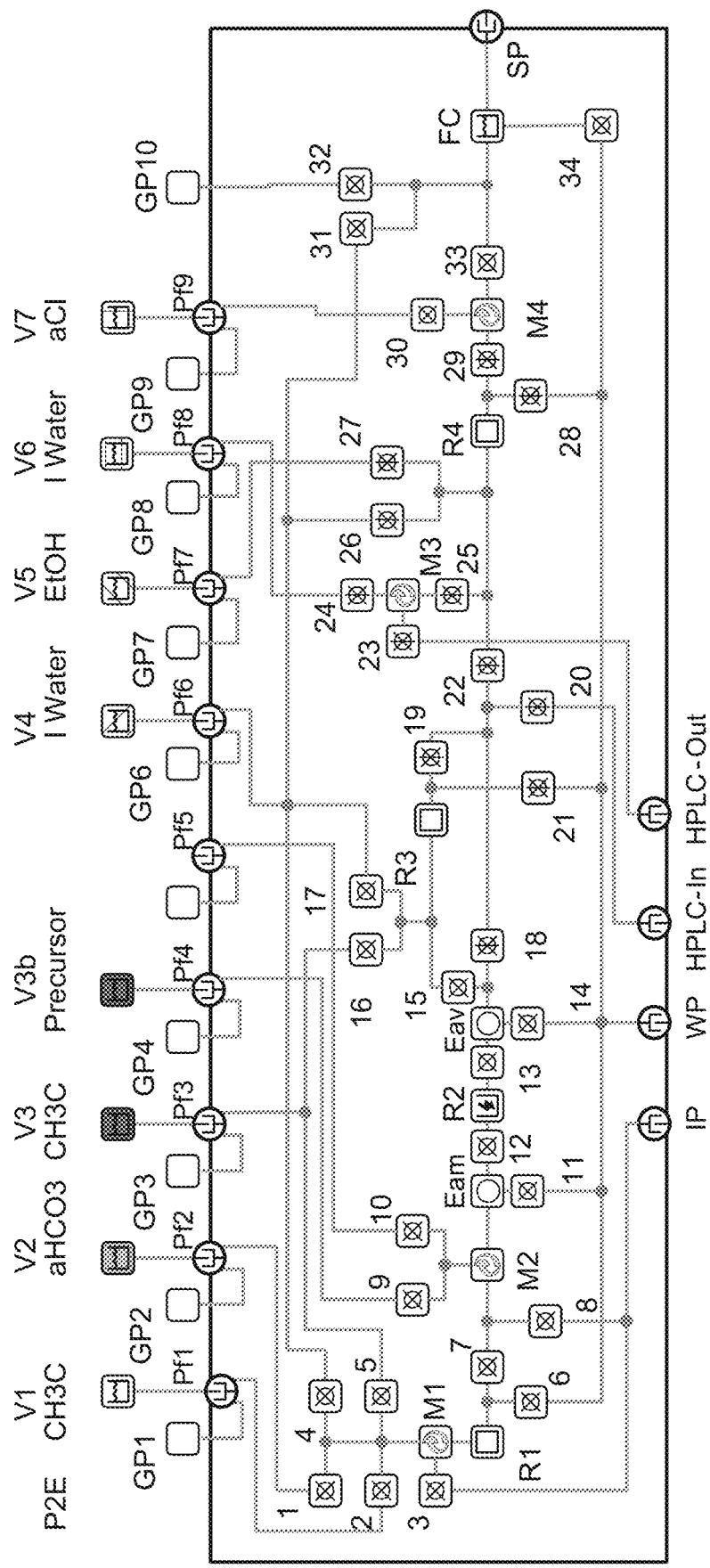
Fig. 3.1

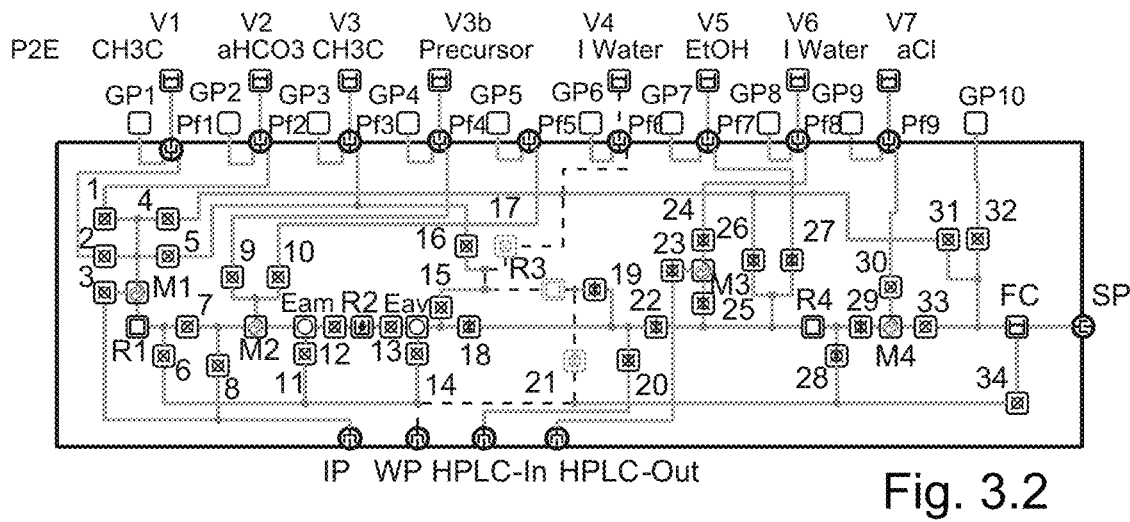
Fig. 3.2
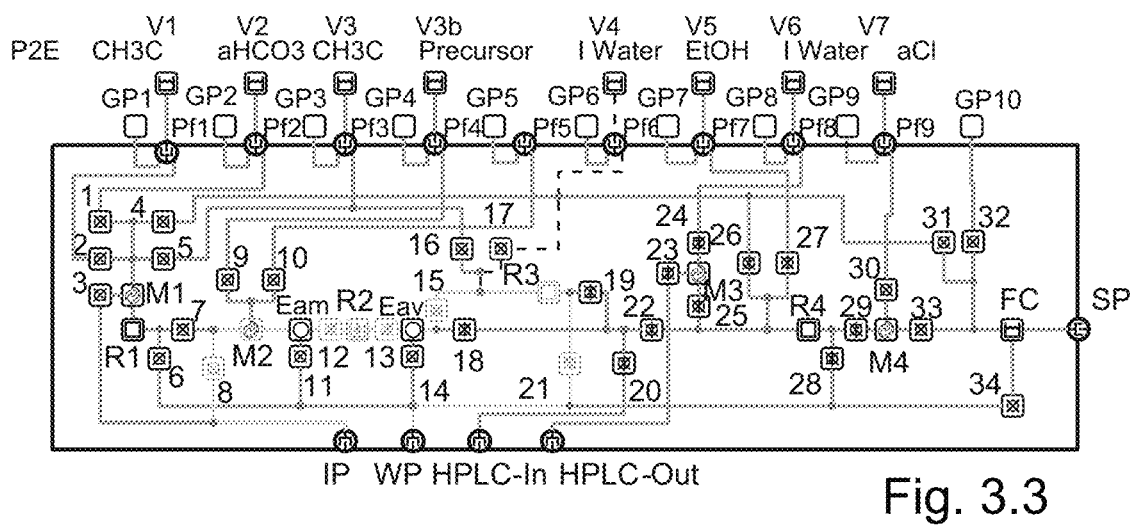
Fig. 3.3
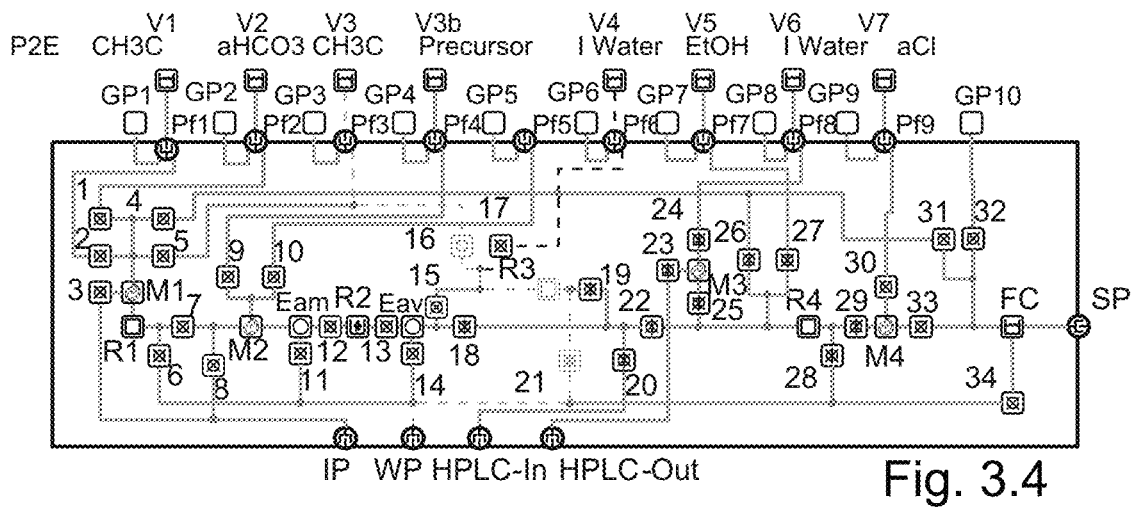
Fig. 3.4

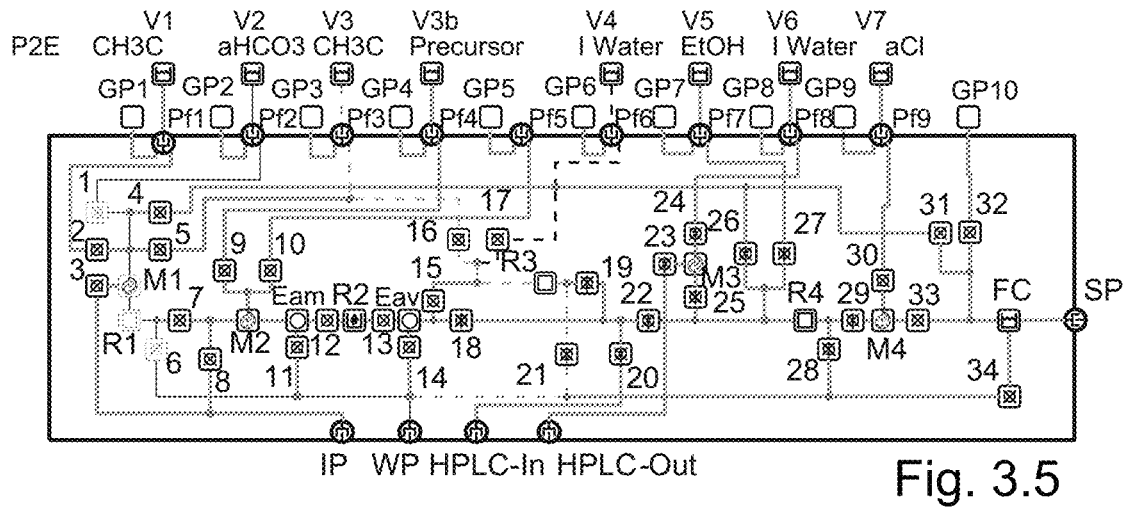
Fig. 3.5
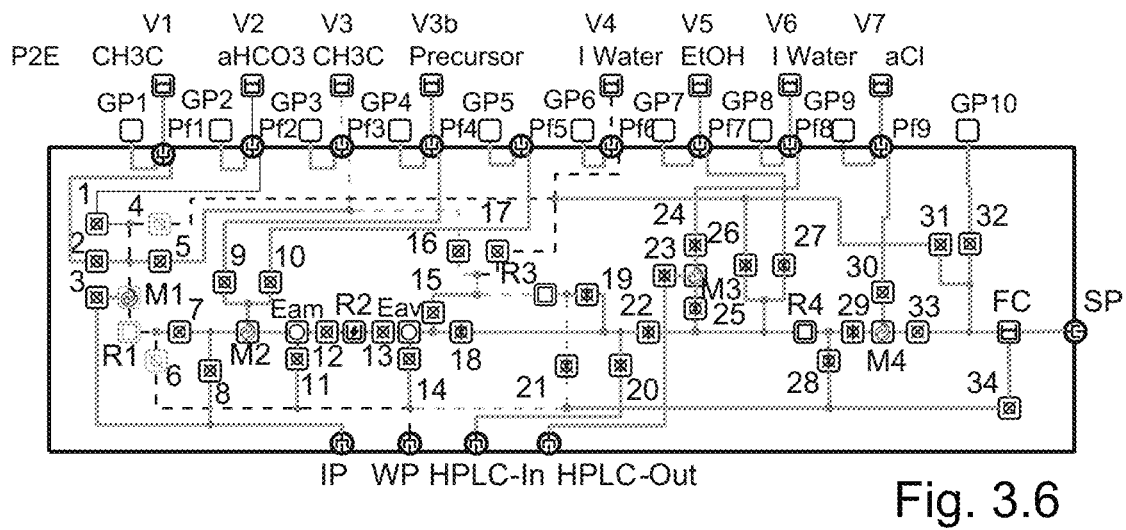
Fig. 3.6
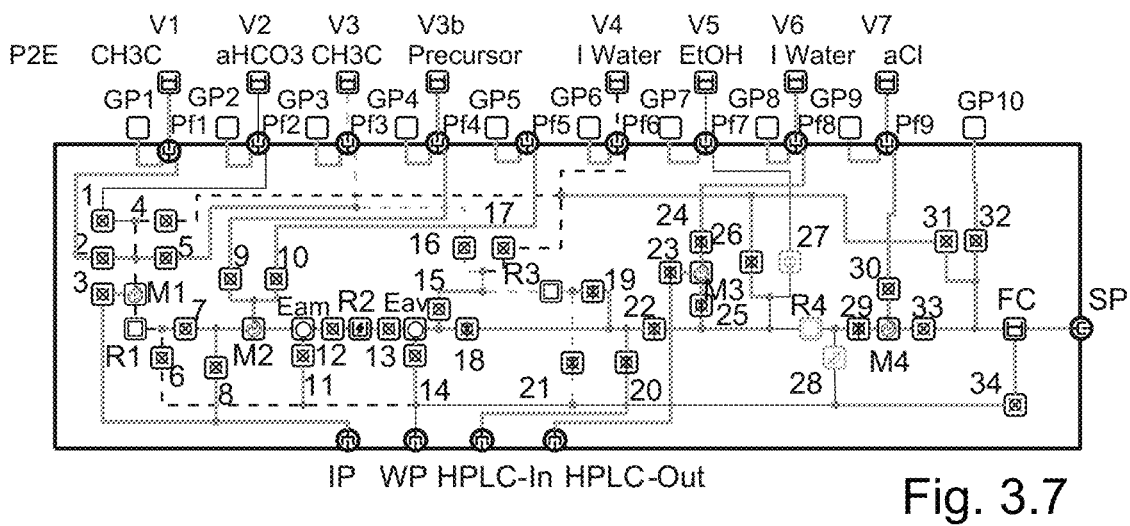
Fig. 3.7

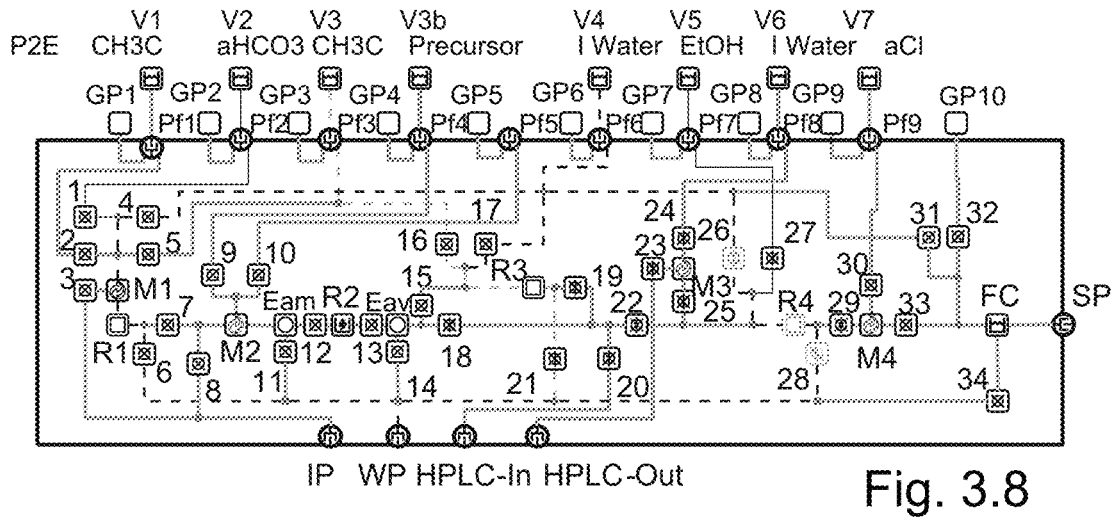
Fig. 3.8
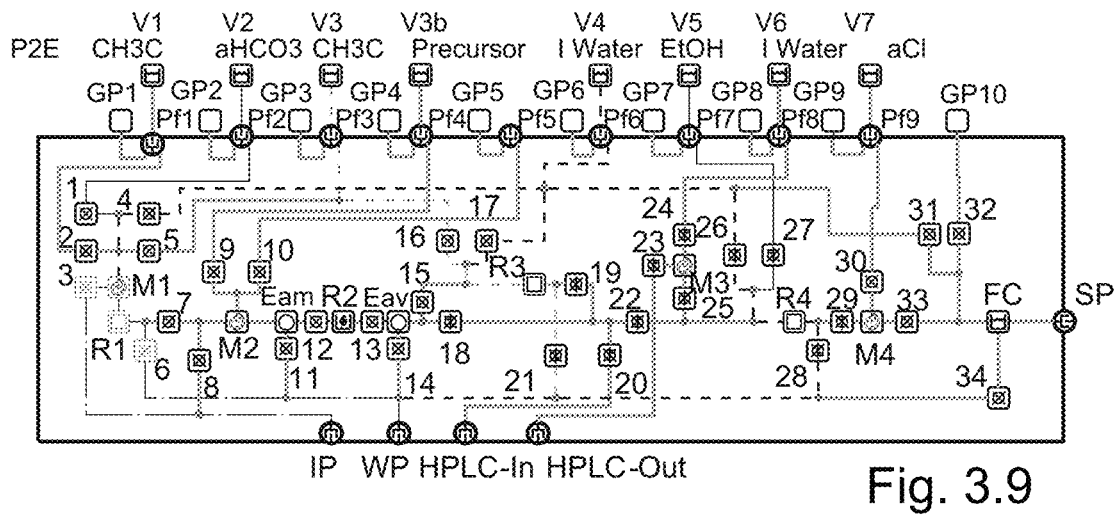
Fig. 3.9
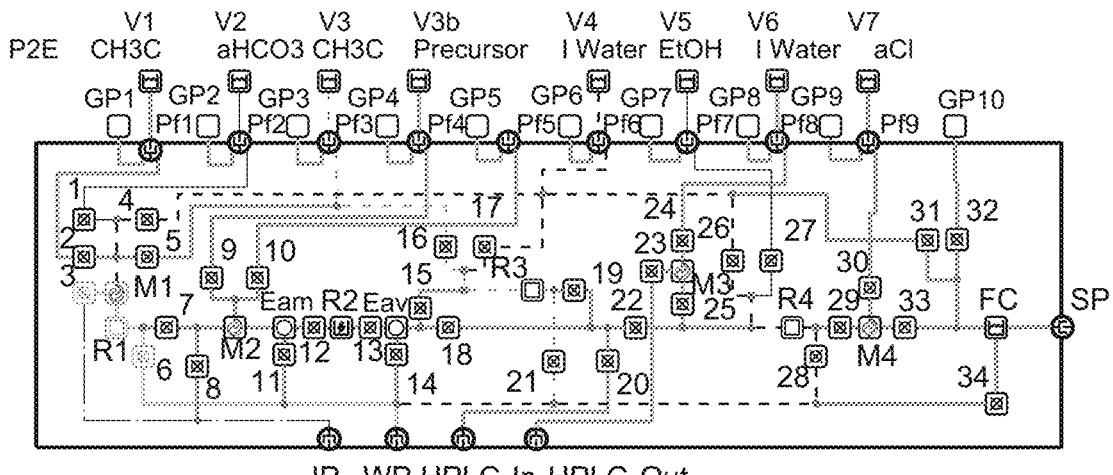
Fig. 3.10

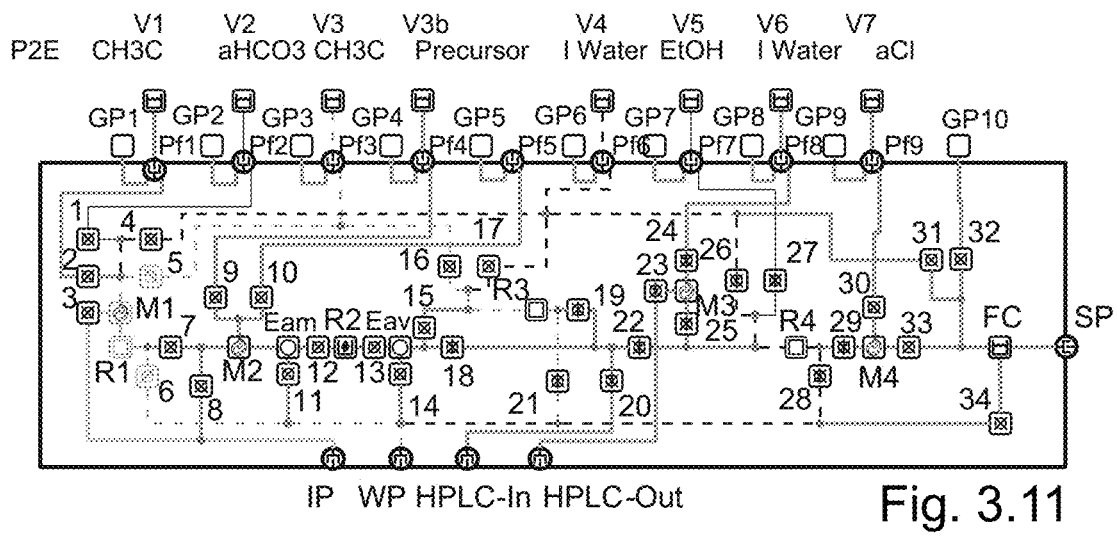
Fig. 3.11
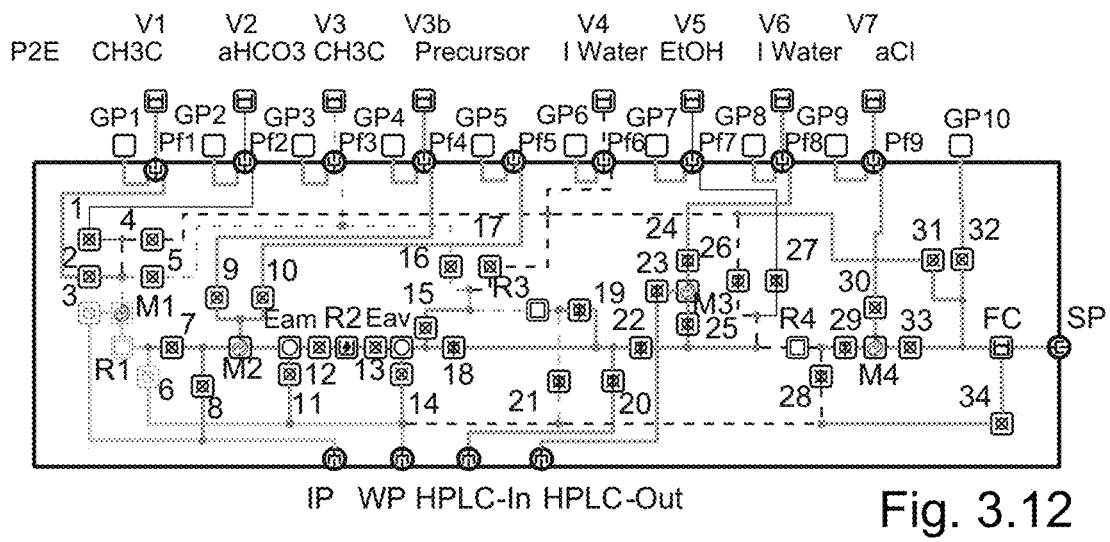
Fig. 3.12
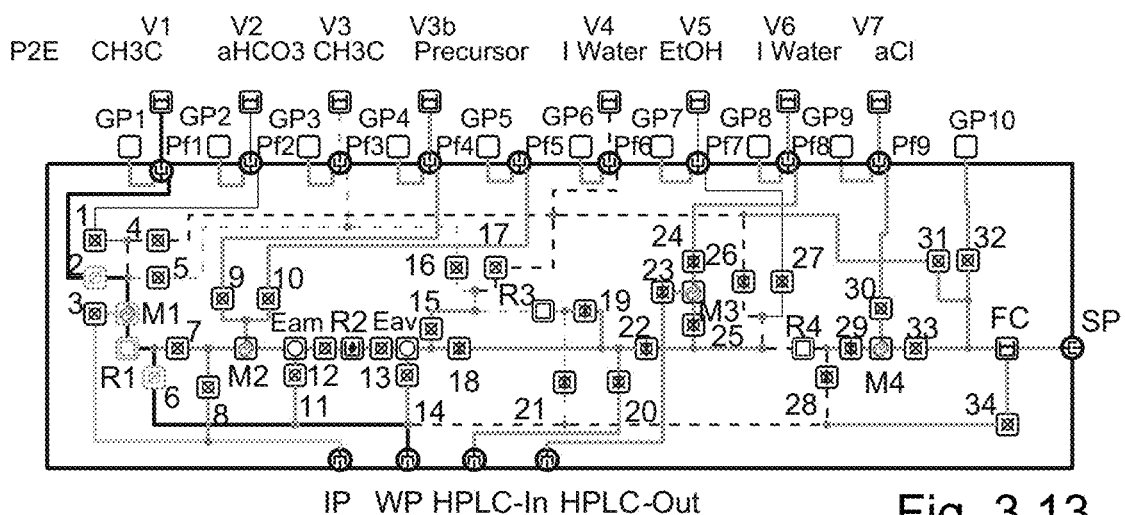
Fig. 3.13

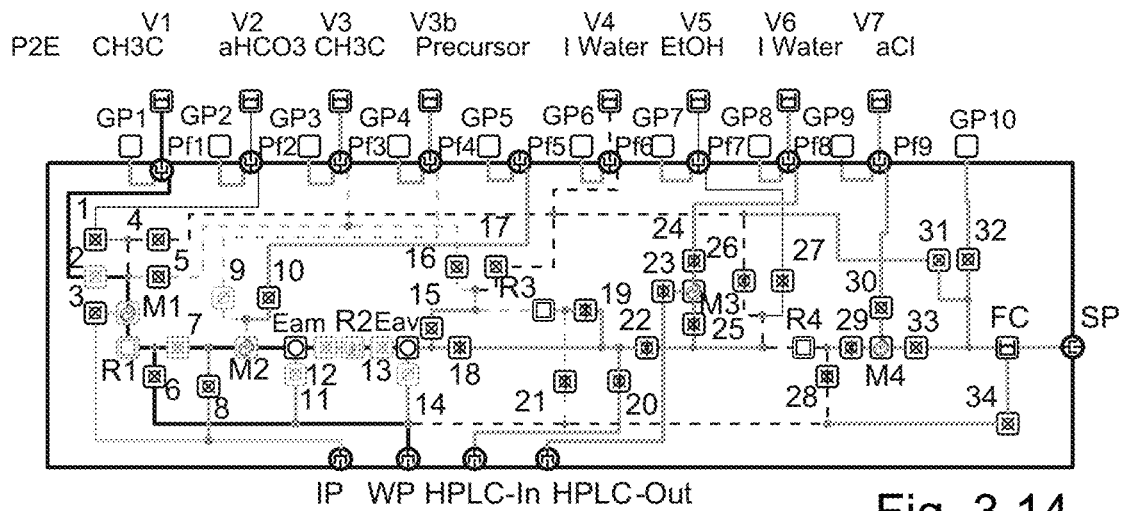
Fig. 3.14
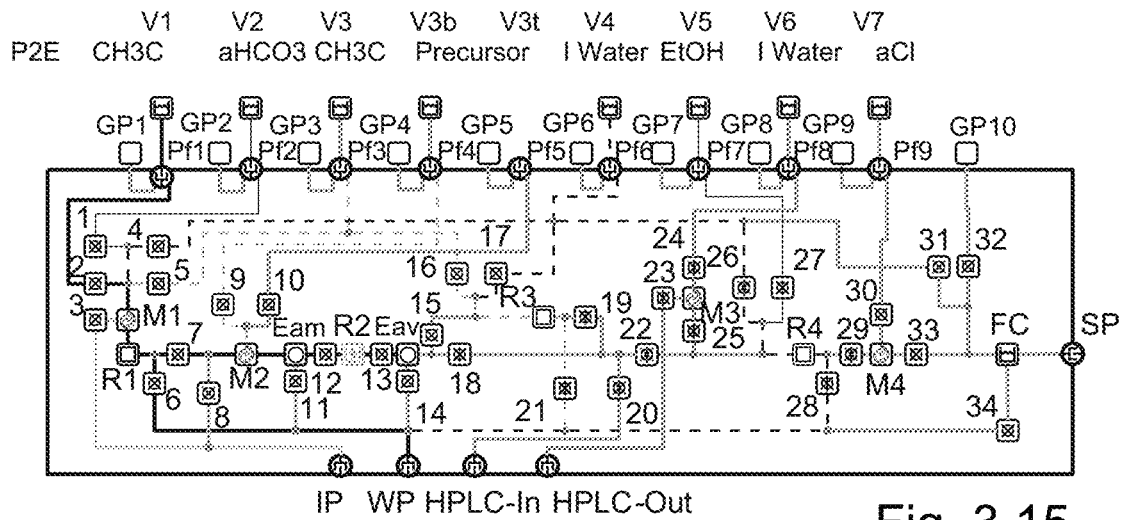
Fig. 3.15
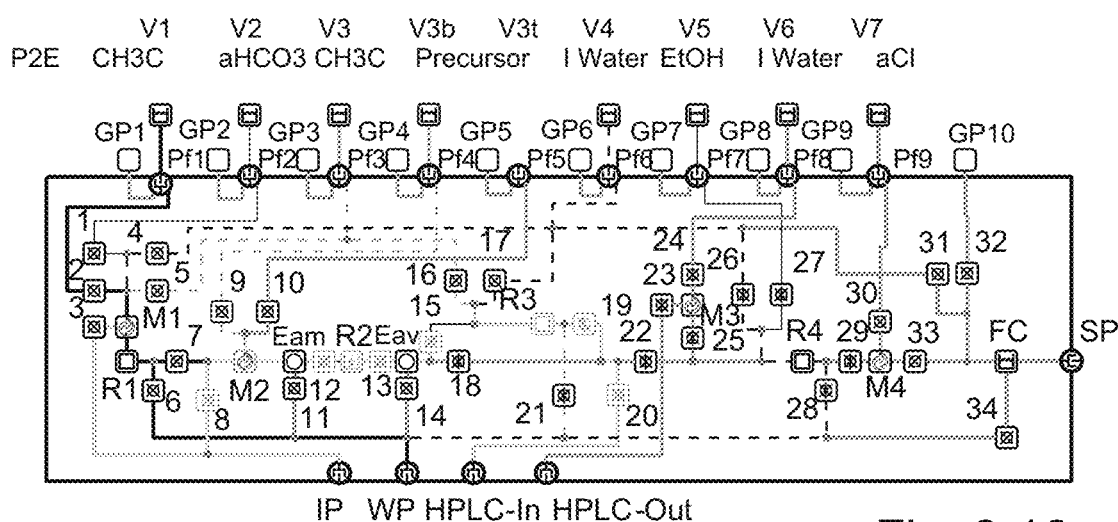
Fig. 3.16

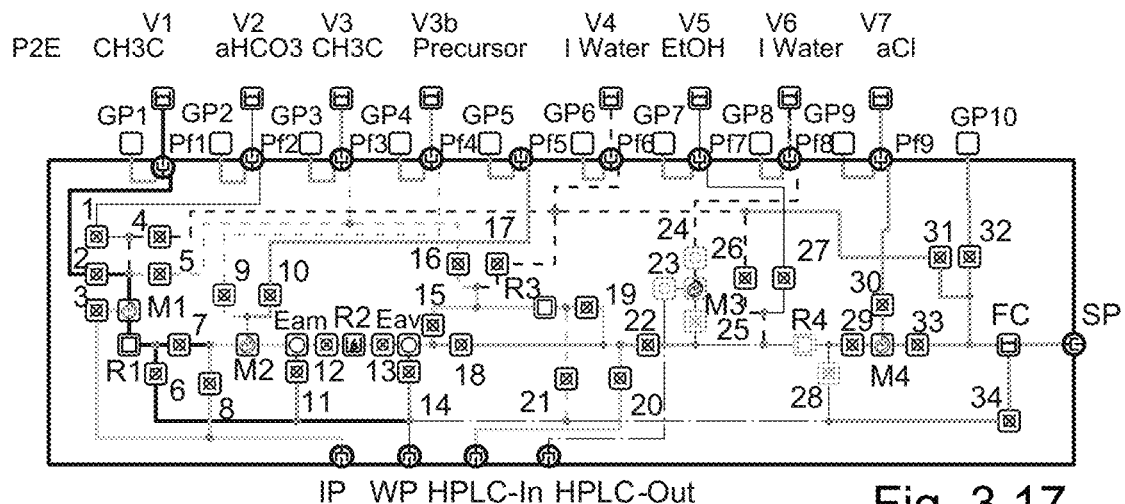
Fig. 3.17
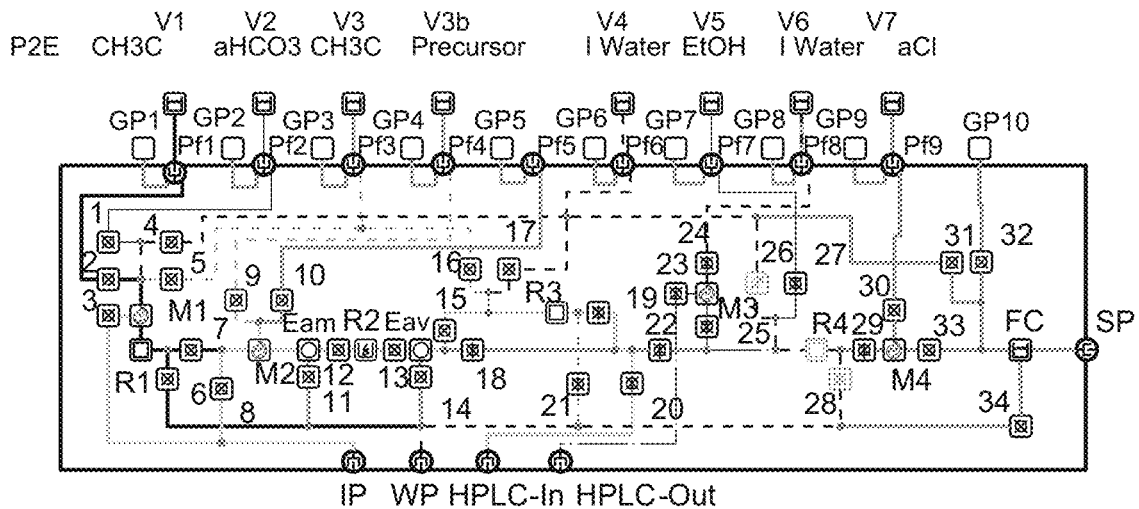
Fig. 3.18
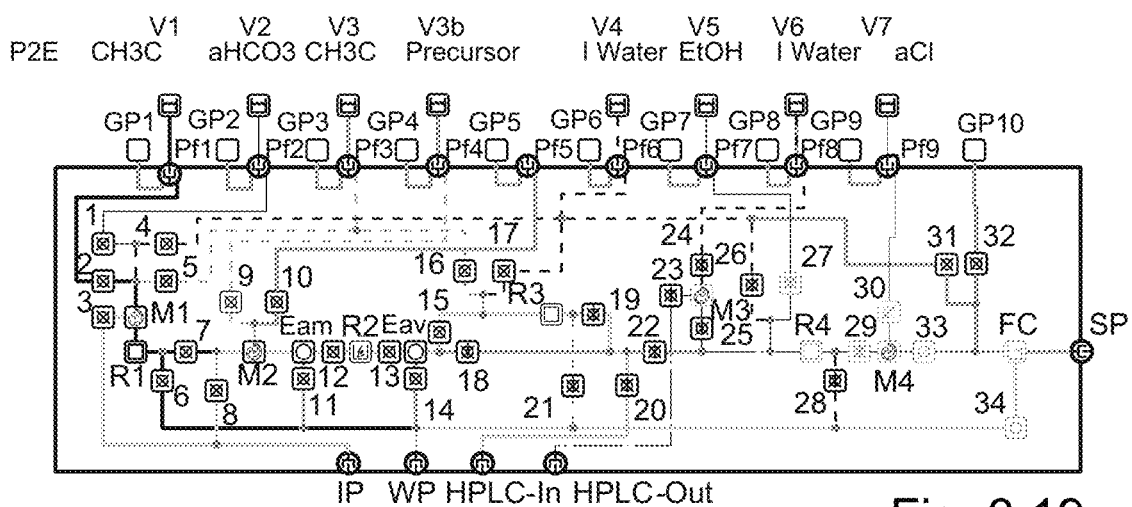
Fig. 3.19

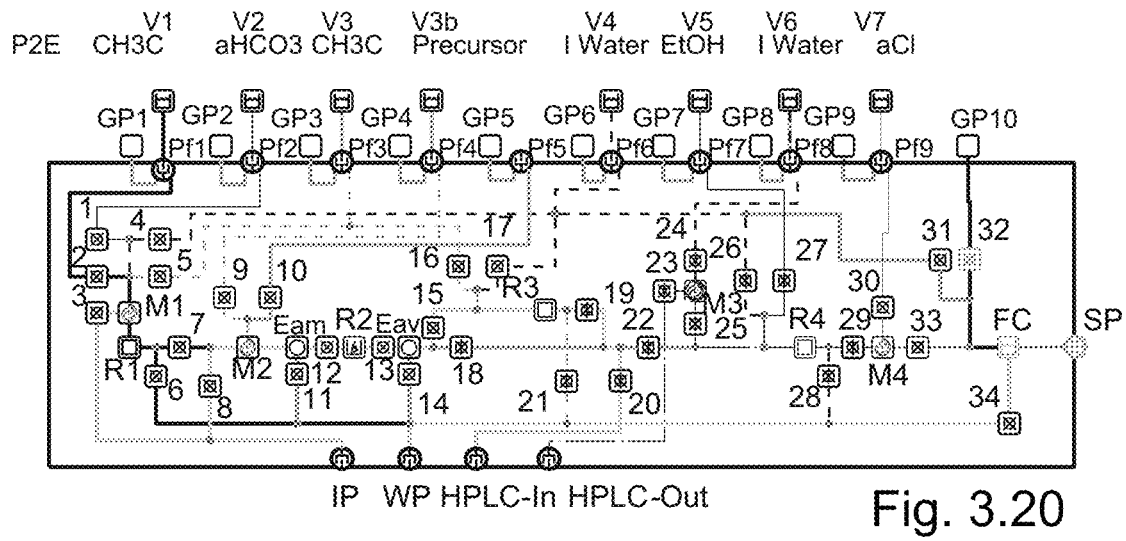
Fig. 3.20
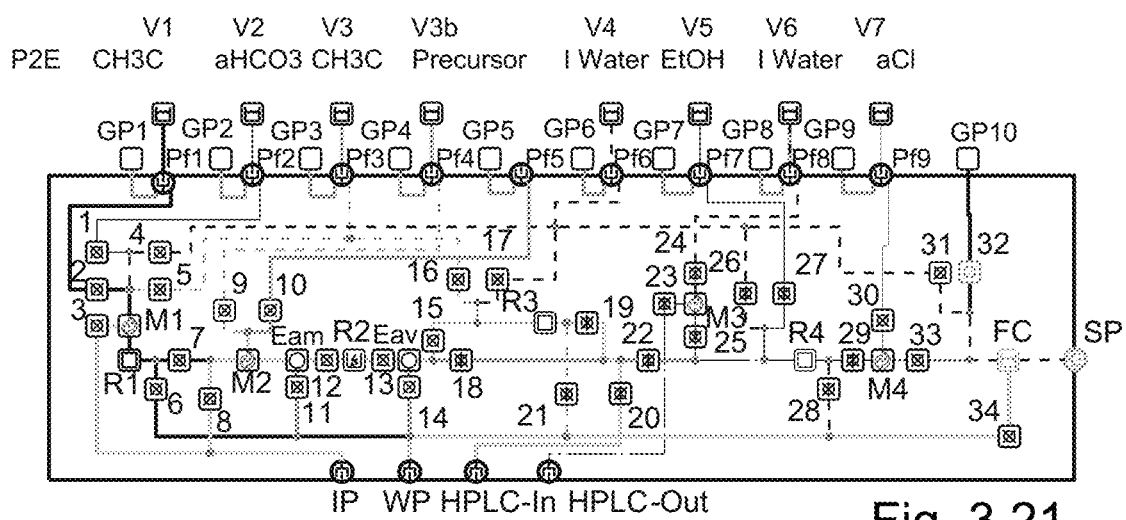
Fig. 3.21
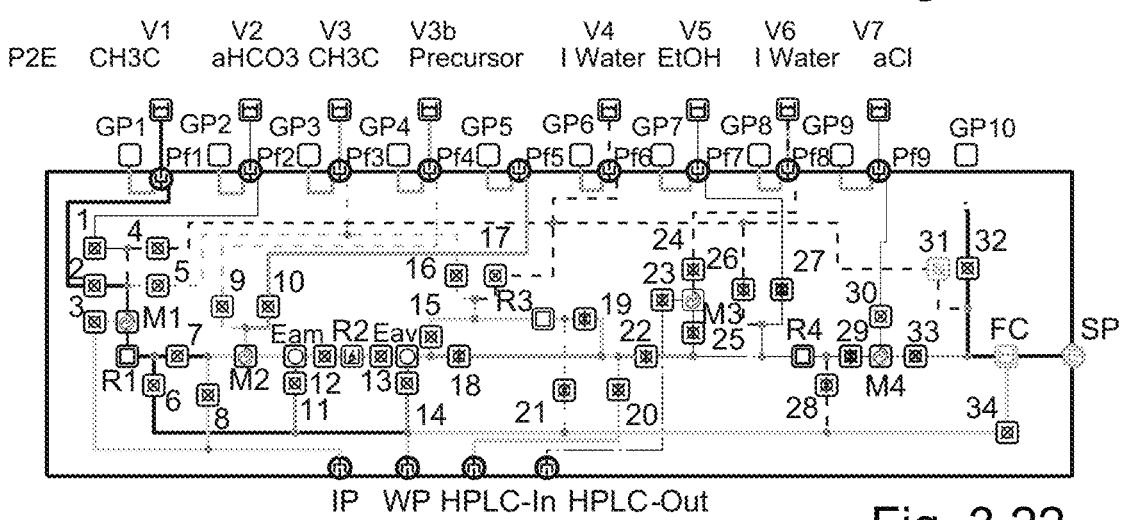
Fig. 3.22

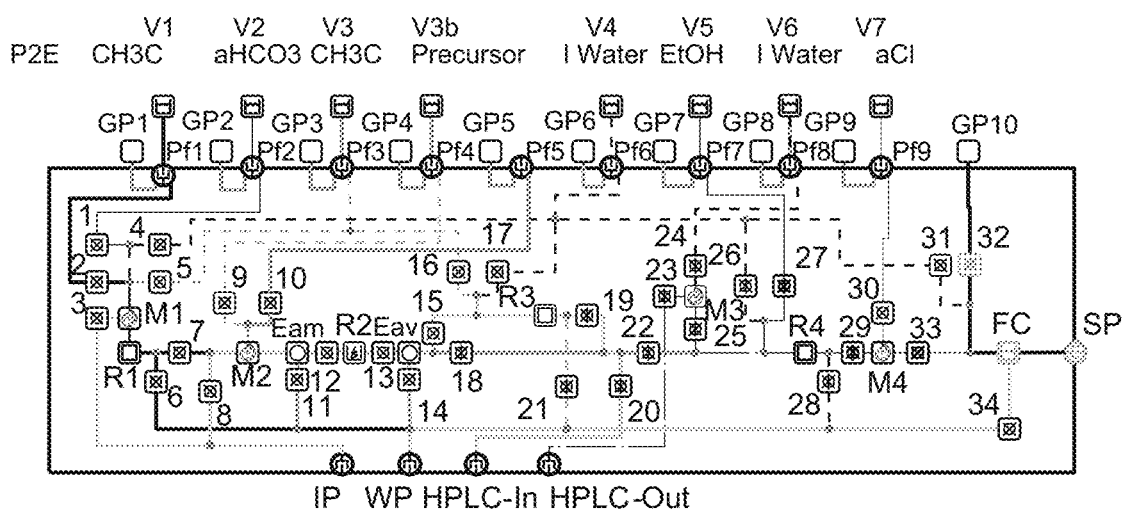
Fig. 3.23

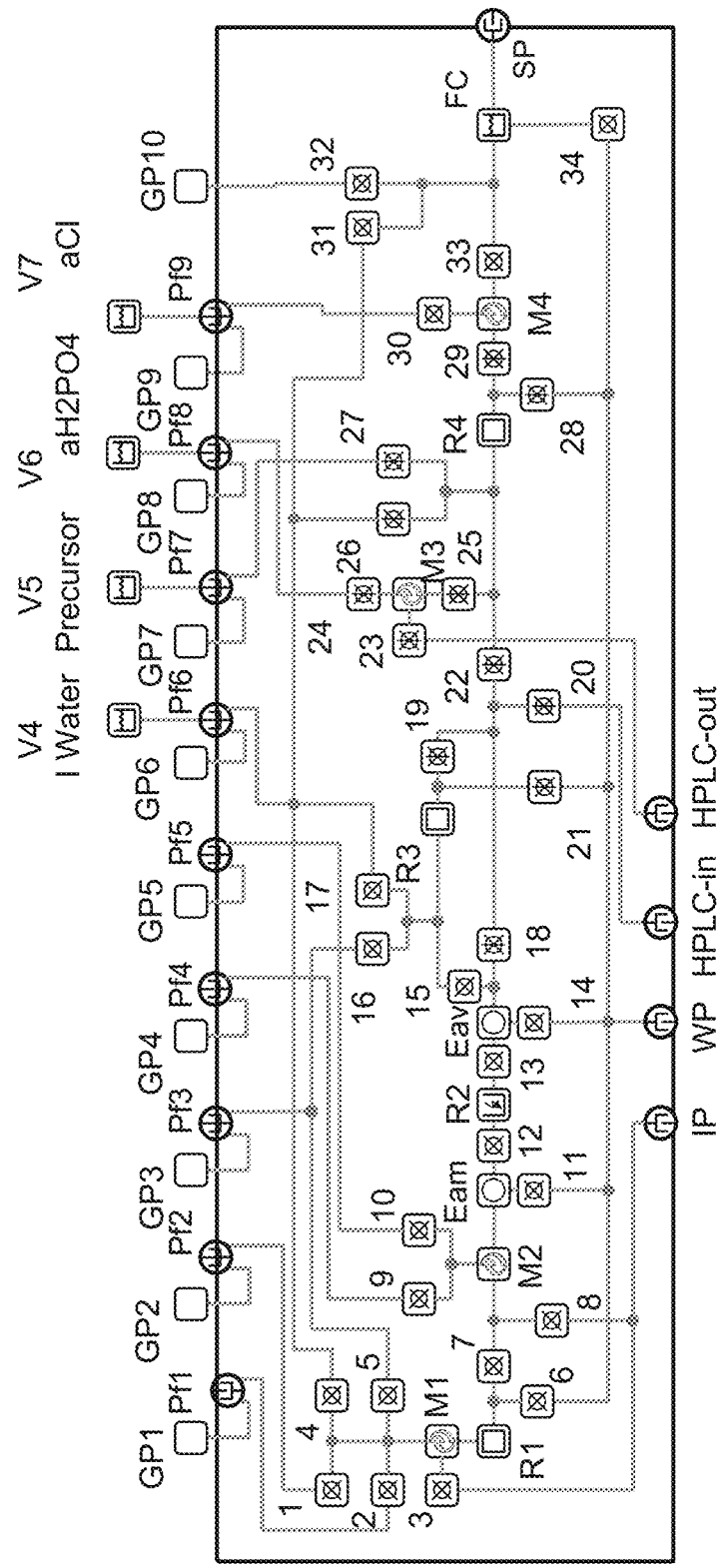
Fig. 4.1

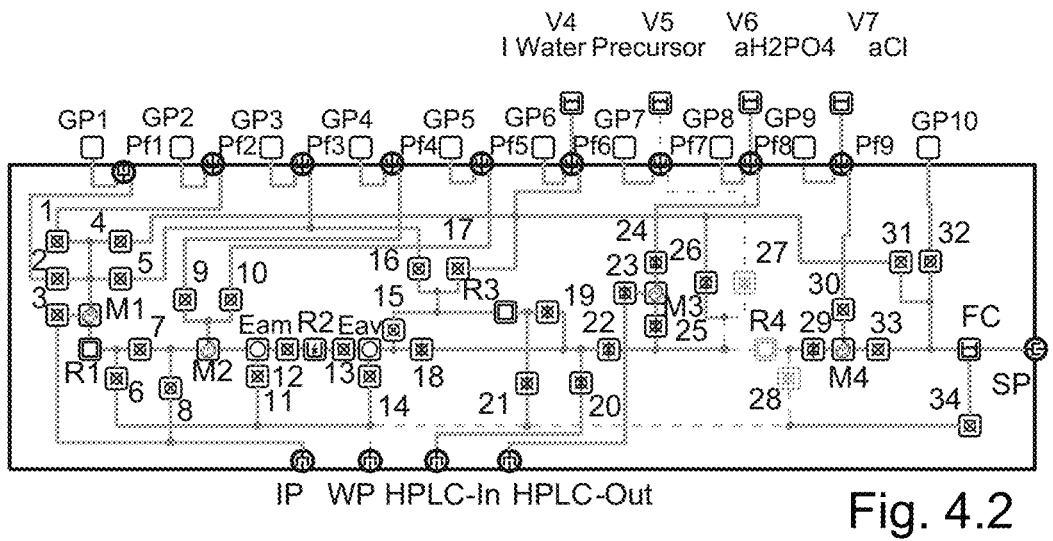
Fig. 4.2
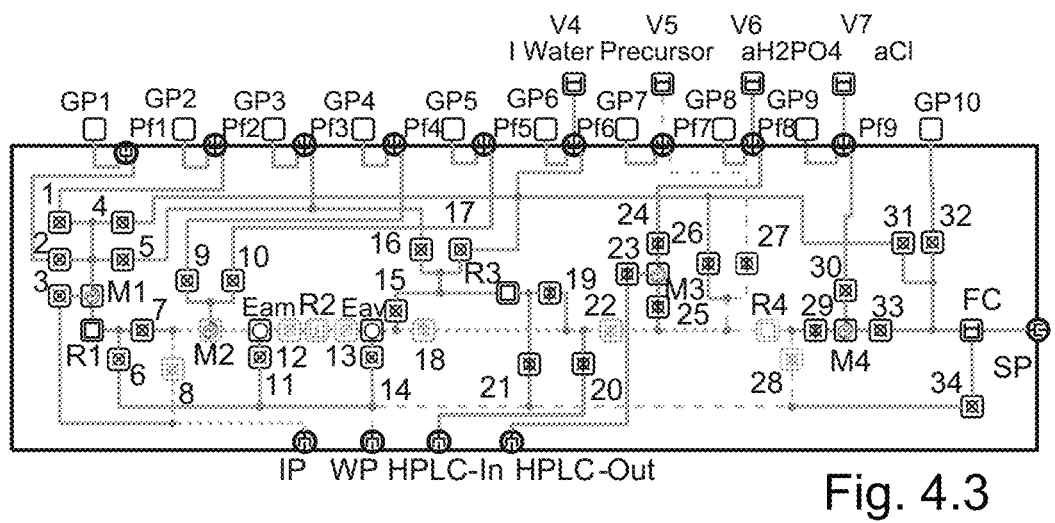
Fig. 4.3
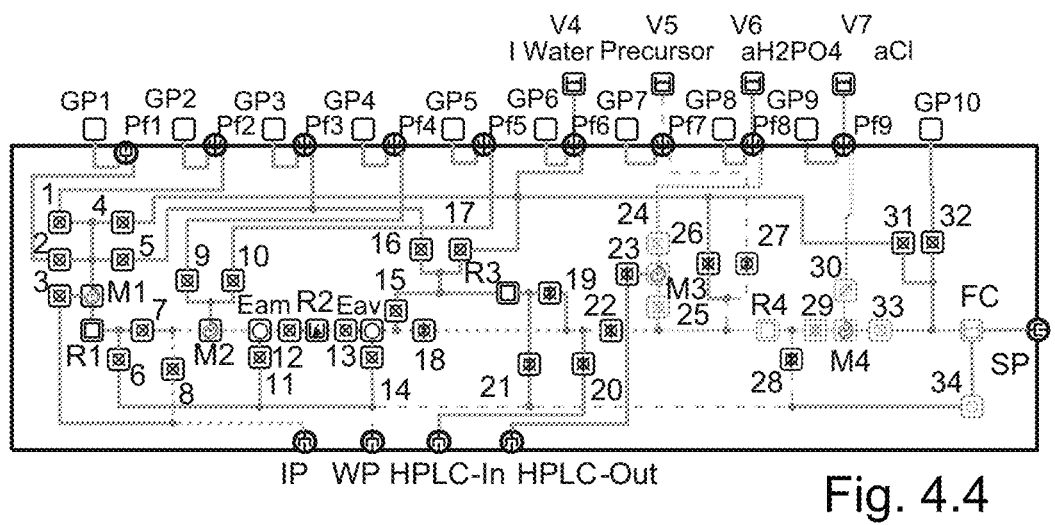
Fig. 4.4

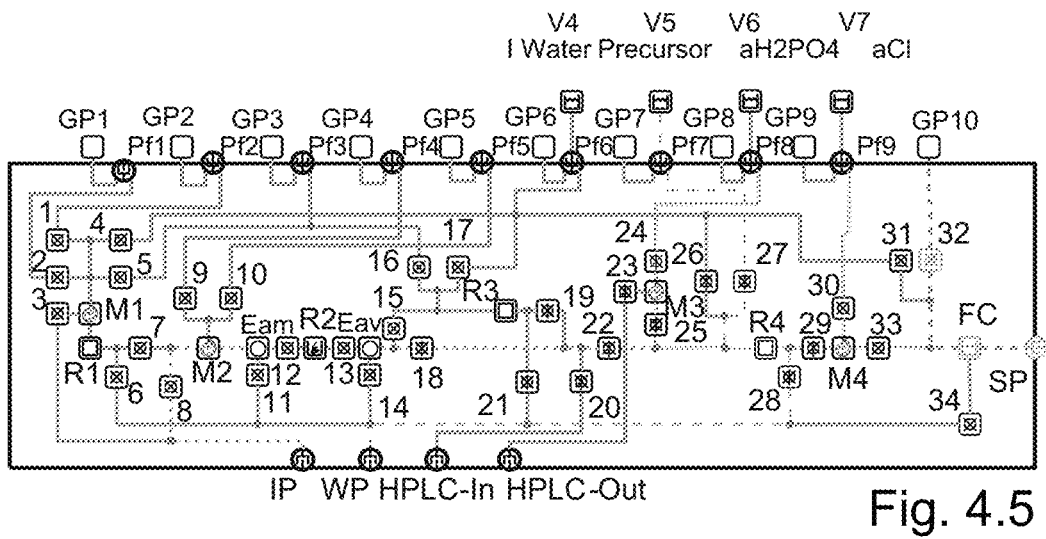
Fig. 4.5
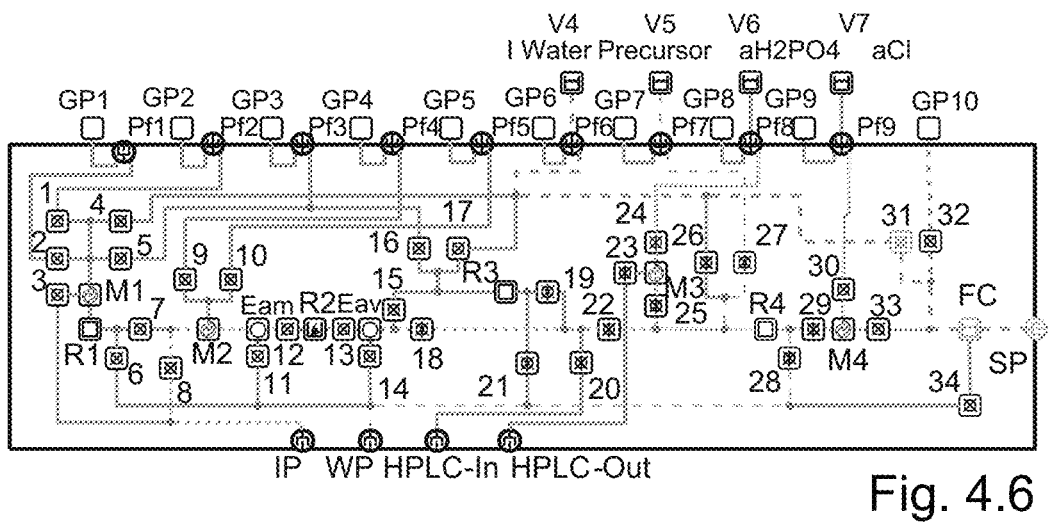
Fig. 4.6
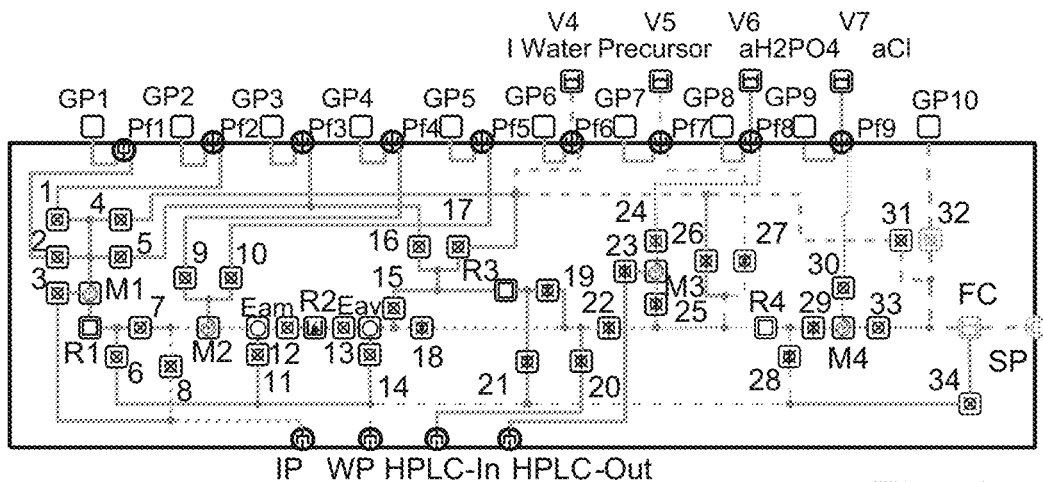
Fig. 4.7

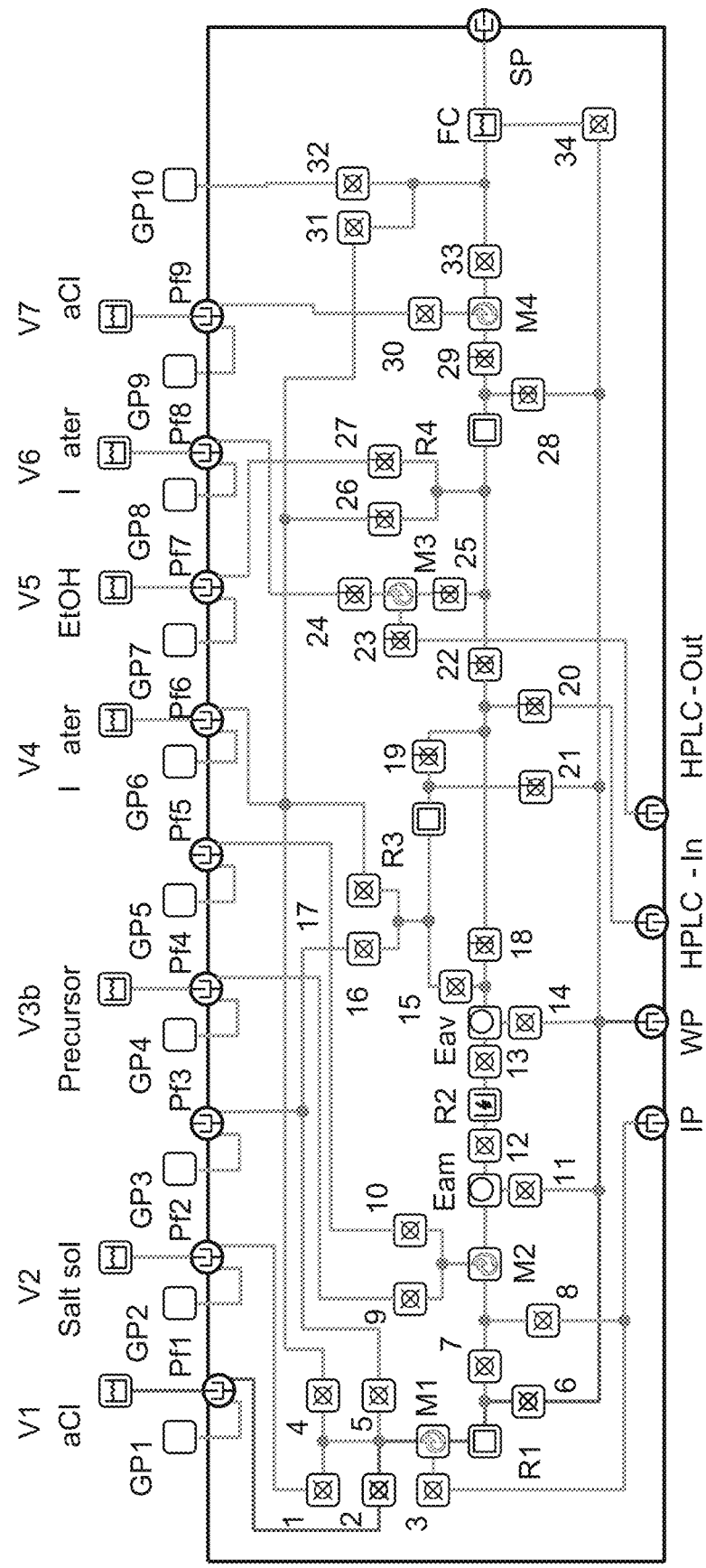
Fig 5.1

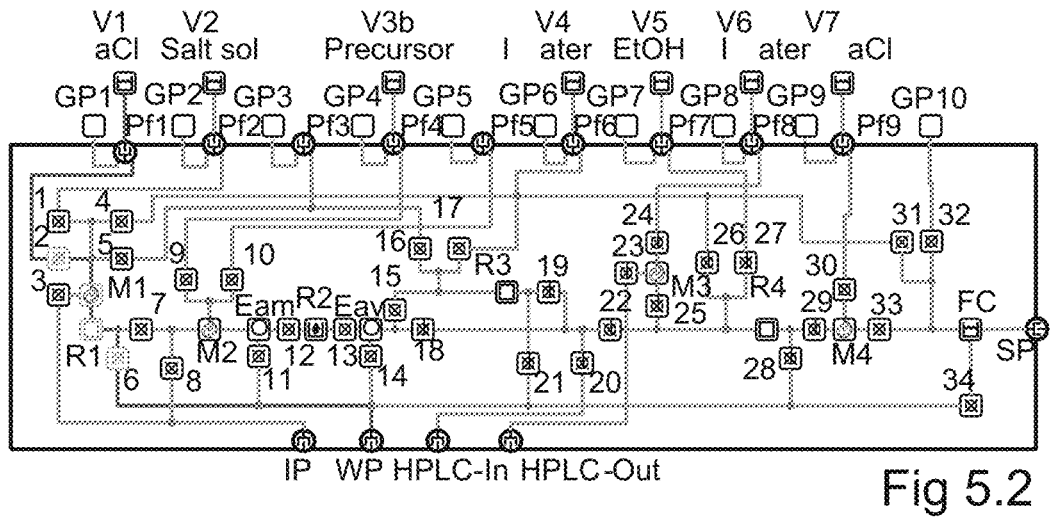
Fig 5.2
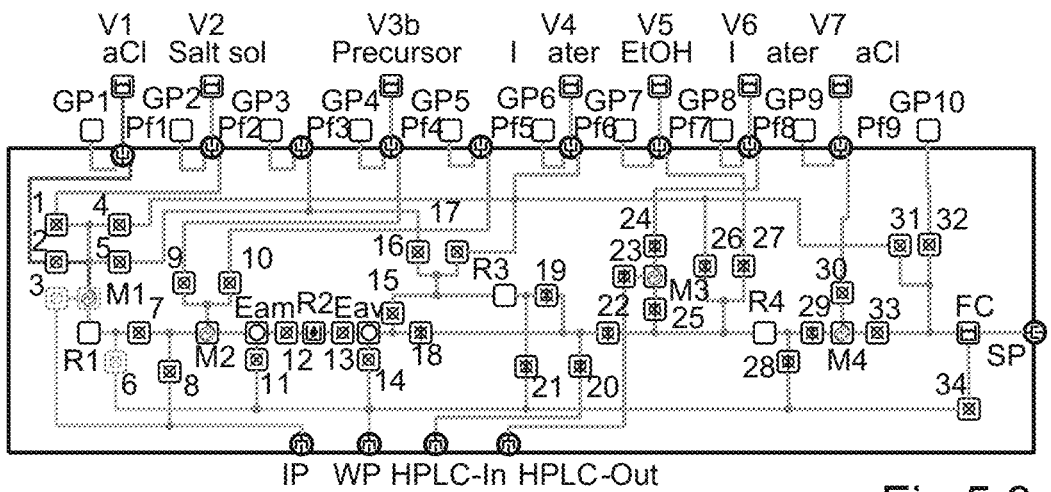
Fig 5.3
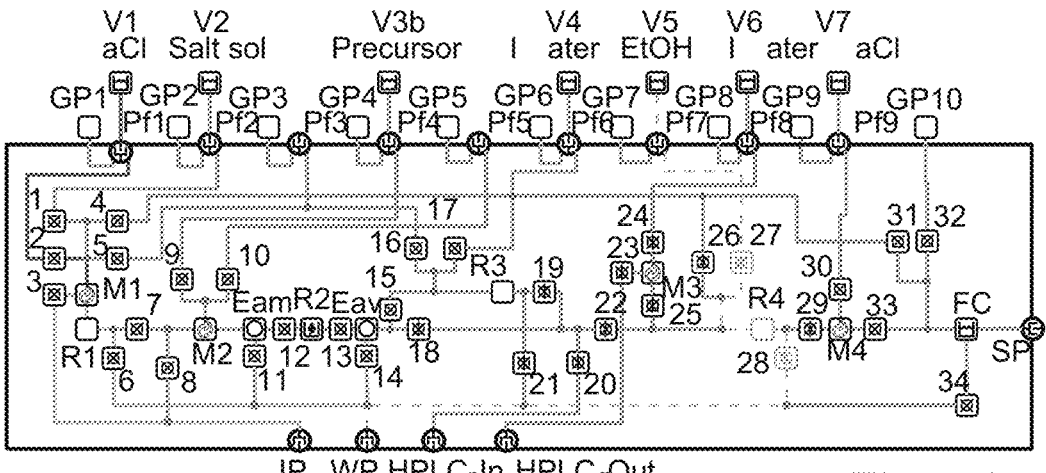
Fig 5.4

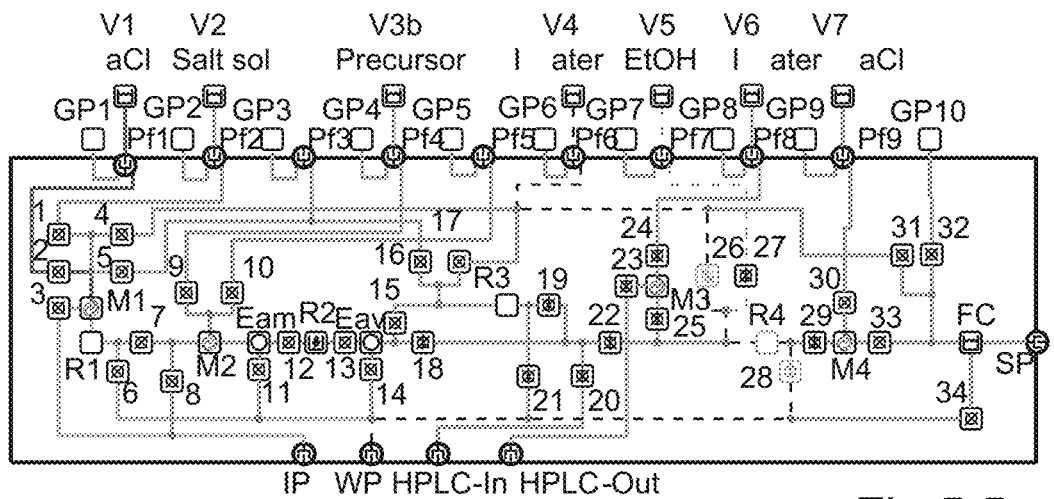
Fig 5.5
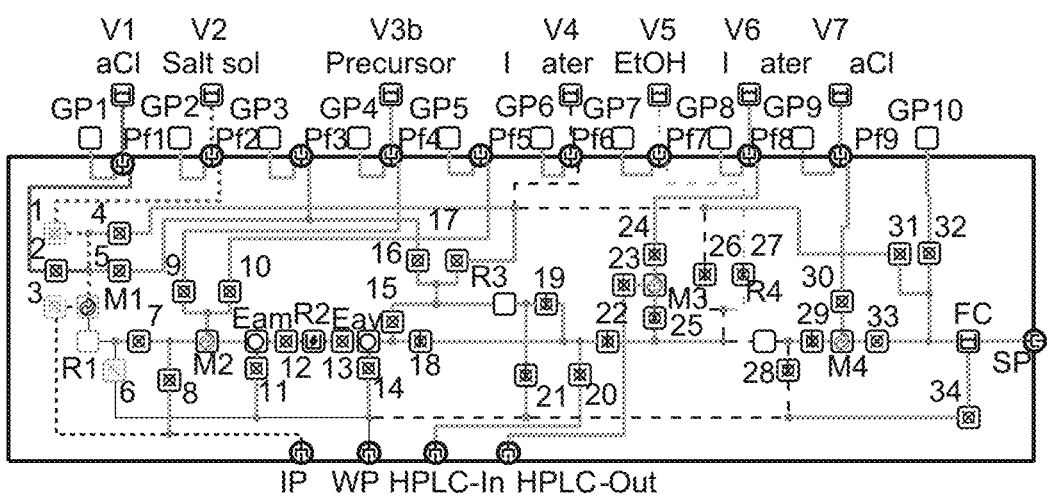
Fig. 5.6
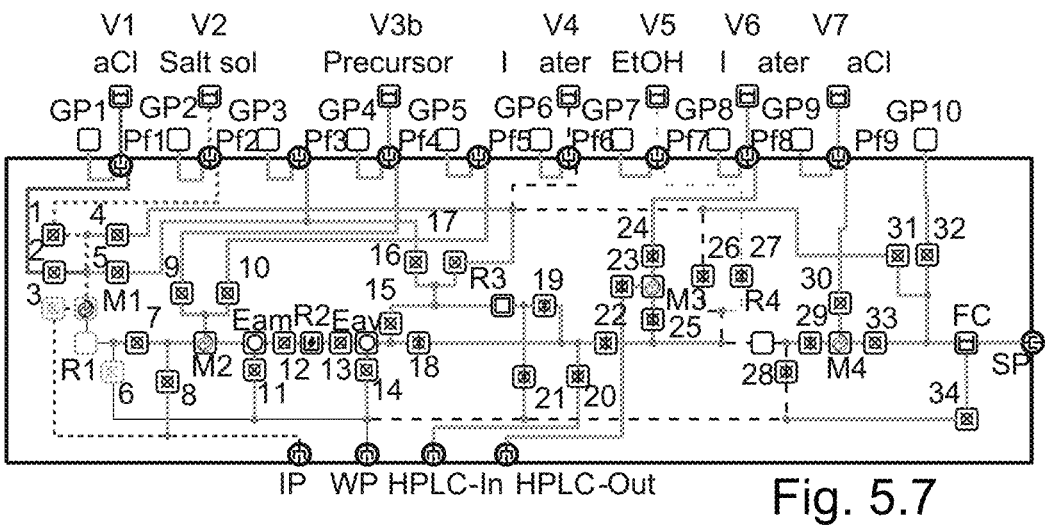
Fig. 5.7

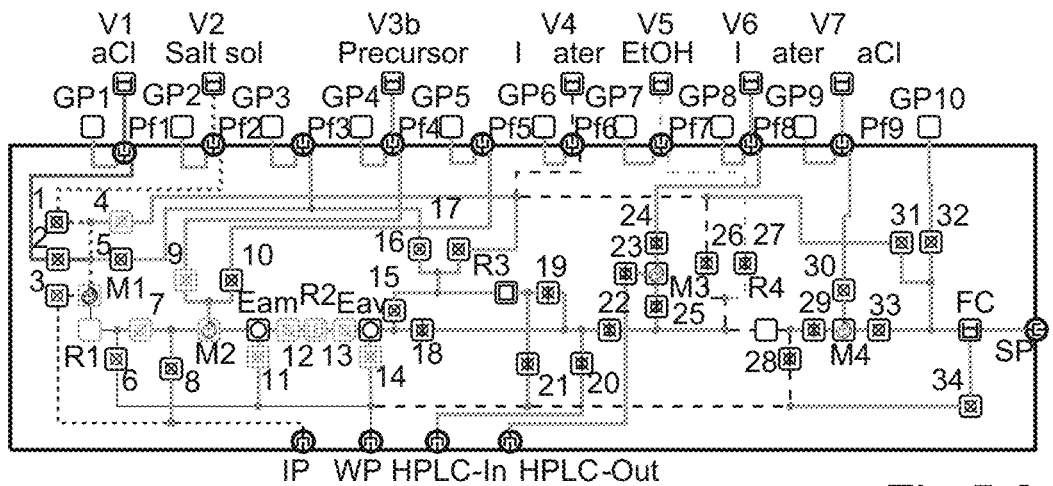
Fig 5.8
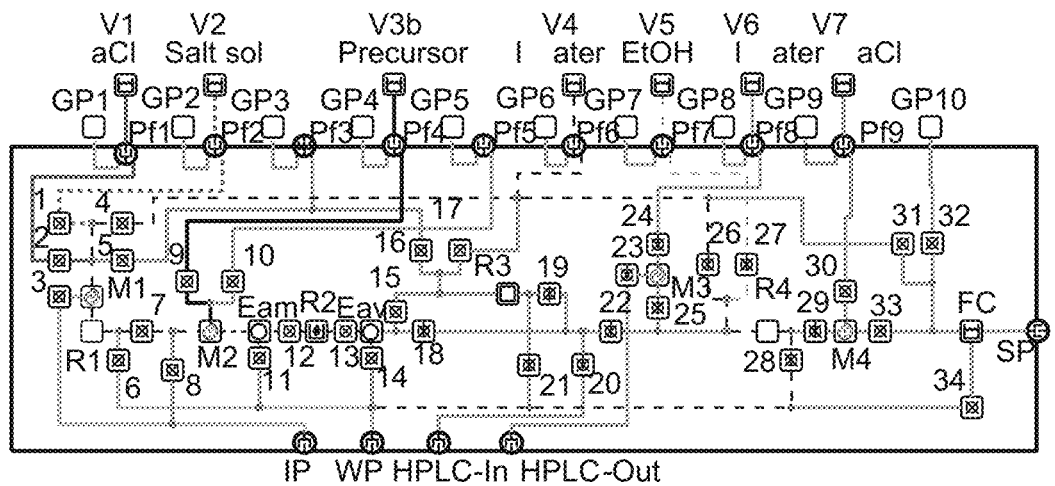
Fig 5.9
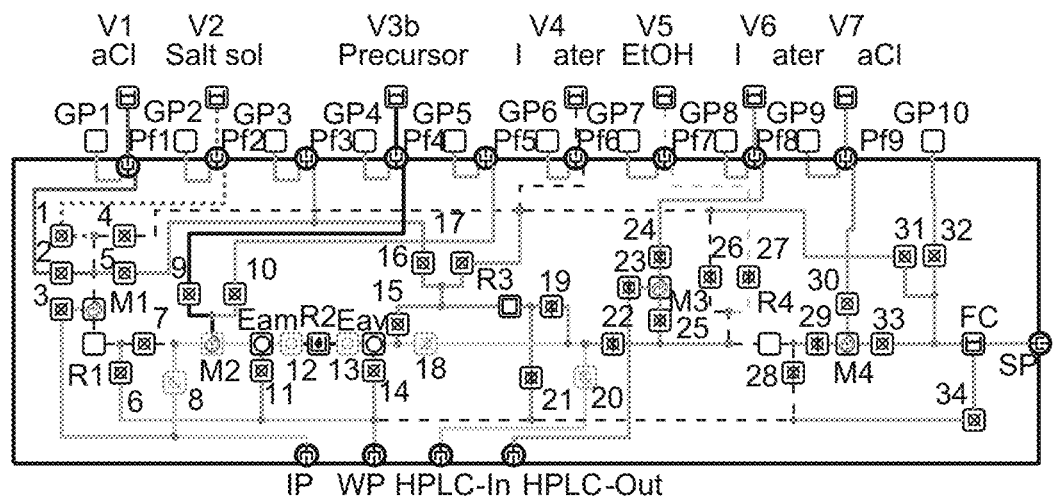
Fig 5.10

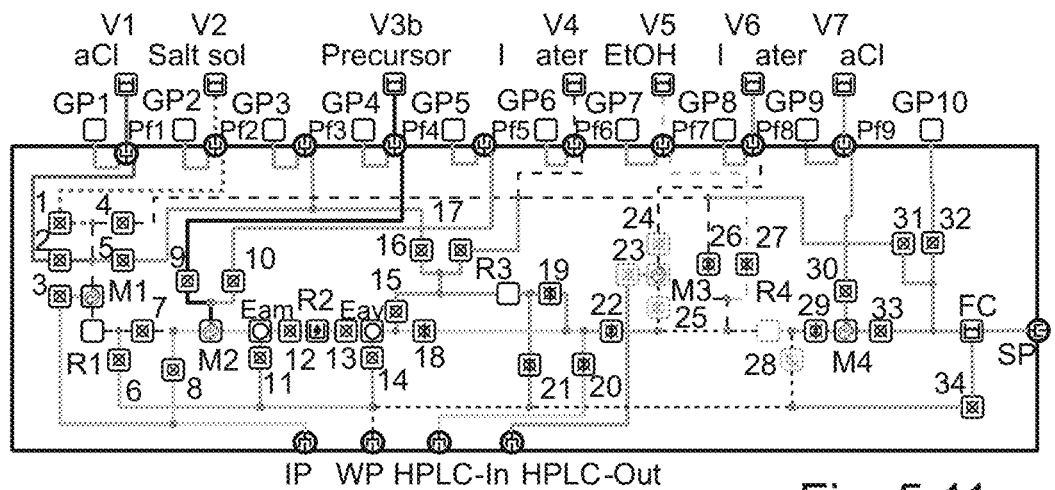
Fig. 5.11
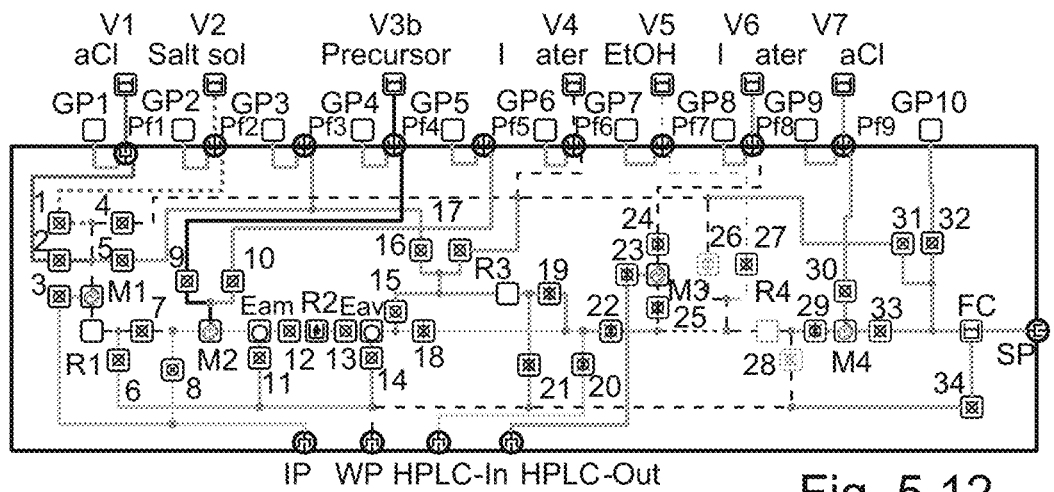
Fig. 5.12
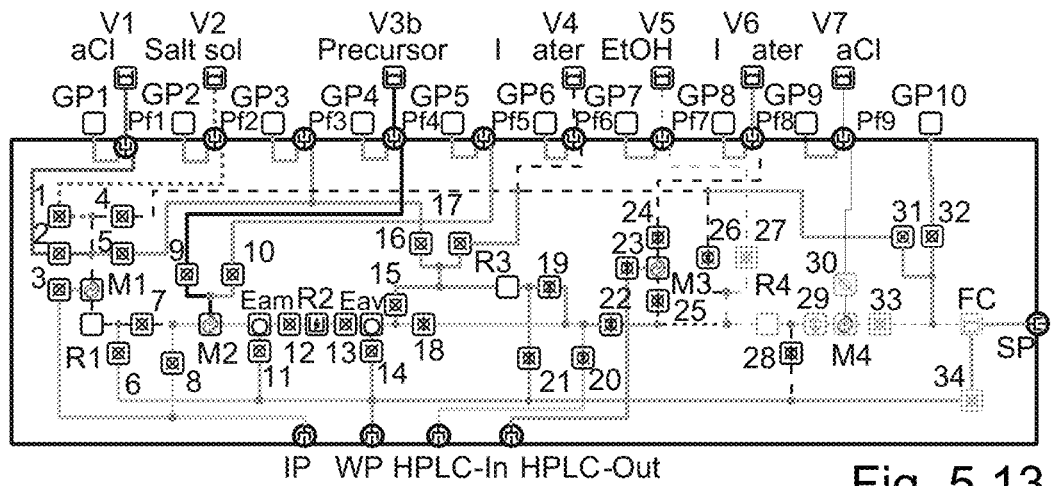
Fig. 5.13

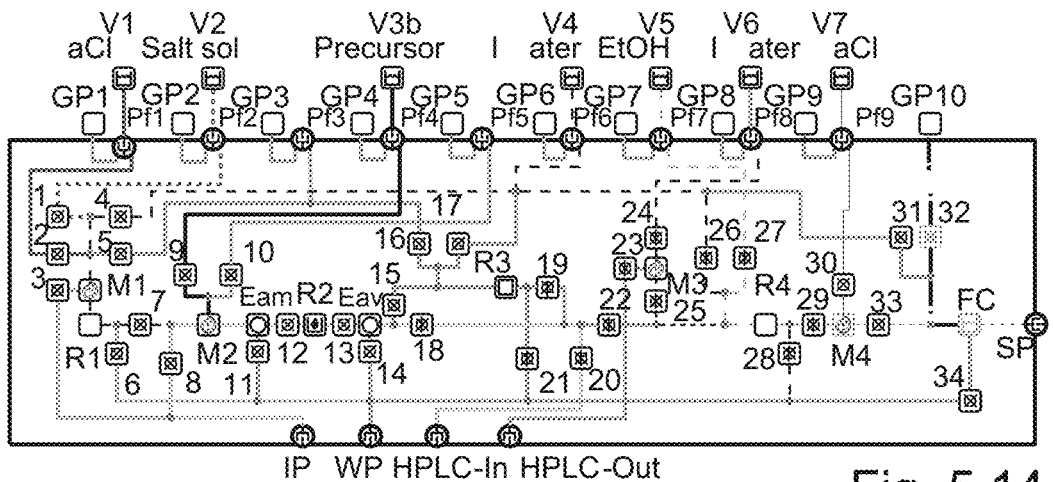
Fig. 5.14
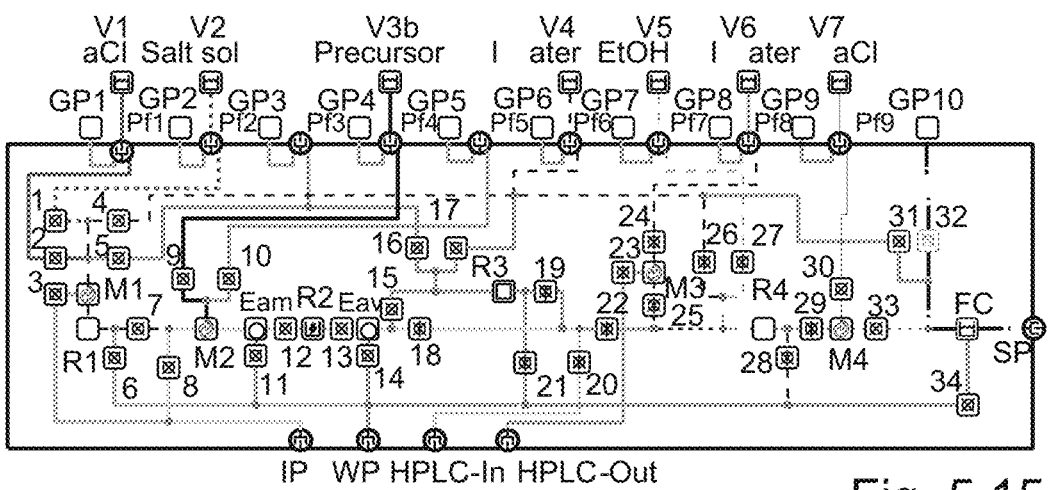
Fig. 5.15
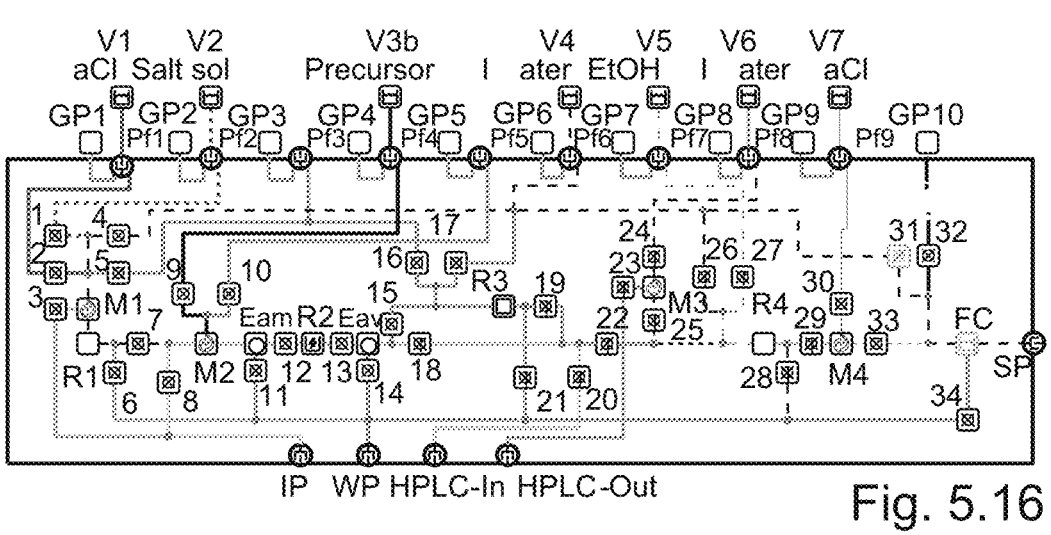
Fig. 5.16

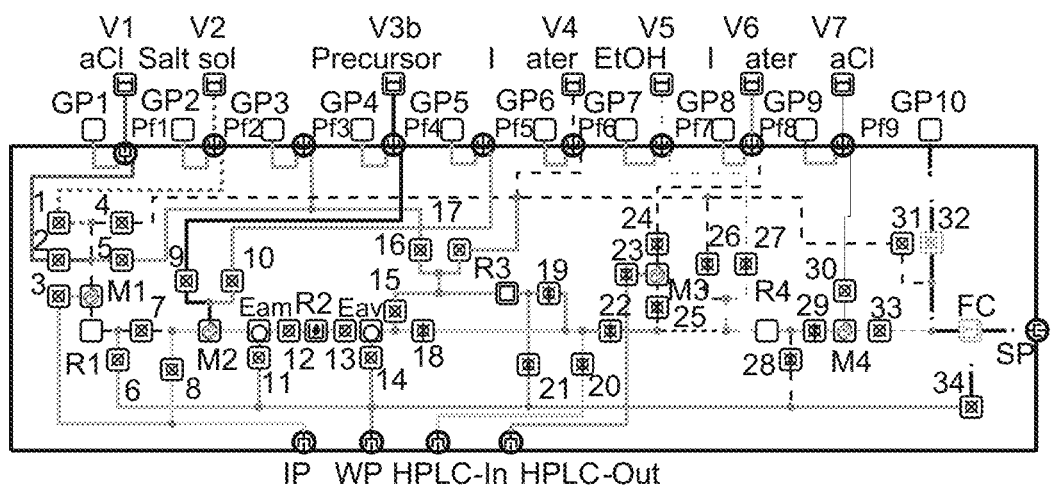
Fig. 5.17

MICROFLUIDIC CASSETTE FOR SYNTHESIZING A RADIO-TRACER AND METHOD OF SYNTHESIZING A RADIO-TRACER WITH SUCH A CASSETTE

This application is a national stage application of International Application No. PCT/FR2018/052540, now WO 2019/077238, filed on Oct. 12, 2018, which claims priority to French Patent Application No. FR 1759802 filed on Oct. 18, 2017.

The present application concerns a microfluidic cassette for synthesizing a radioactive tracer.

BACKGROUND OF THE INVENTION

A current radiochemistry cassette relies on the use of different commercially-available macroscopic components, which are for example mechanical valves, bead columns, vials, etc., which are assembled together to enable radio-synthesis to be carried out, that is to say the synthesis of a radioactive tracer, which is a radioactive pharmaceutical molecule associating a molecule of pharmaceutical interest with a radioisotope.

Such a cassette is mainly designed for the production of a large quantity of a single product which is then distributed to several hospitals or care centers for example.

It moreover is of imposing total volume. The various components are not optimized to produce small quantities of radioactive tracers, for example for a single patient.

They therefore lead to using an excessive amount of reagents and radioisotopes to promote the result of the reaction, that is to say the synthesis of a desired radioactive tracer. Furthermore, such components have high dead volumes and their size means that a high level of radioactivity remains in the cassette after the synthesis, prohibiting manipulation of the cassette by an operator for many hours, according to the half-life of the radioisotope used.

Lastly, such a cassette then constitutes a voluminous item of radioactive waste.

Application WO 2016/166486 for example describes a cassette enable the aforementioned drawbacks to be overcome, at least in part, while furthermore leading to other advantages.

Thus, at least one of the objectives of the present application is to improve such a cassette, while furthermore leading to other advantages.

SUMMARY OF THE INVENTION

To that end, according to a first aspect, there is provided a microfluidic cassette for synthesizing a radioactive tracer comprising:
A mounting card,
A microfluidic circuit, at least partly integrated into the mounting card, comprising:
  at least one connector for supply by a vial, configured to connect a vial to the microfluidic circuit,
  at least one isotope port, configured for introducing a radioisotope into the microfluidic circuit,
  at least one reaction chamber, connected to the at least one connector for supply by a vial and to the at least one isotope port by capillaries,
  at least one mixing chamber, positioned upstream of the at least one reaction chamber and connected to the at least one reaction chamber upstream of which it is positioned by at least one capillary,
  at least one formulation chamber, connected to the at least one isotope port and to the at least one connector for supply by a vial and positioned downstream of the at least one reaction chamber, and
  at least one connector for connecting a syringe, positioned downstream of the at least one formulation chamber and connected to the at least one formulation chamber by at least one capillary; in the context of the present application, a syringe designates any container enabling the radioactive tracer obtained to be collected as output from the cassette; this designation here includes for example a reservoir or a bottle.

Such a mounting card typically measures of the order of around ten centimeters laterally, for example between 10 cm and 30 cm laterally, and less than 7 cm in thickness, or even less than 5 cm in thickness.

In other words, the cassette mainly comprises:
what is referred to as a "microfluidic" part, composed in part of capillaries, i.e. channels of small dimensions (typically of approximately 500 µm (micrometers) in diameter or width), of reaction chambers (each having a volume of the order of the microliter, for example comprised between 10 µL and 500 µL), of mixing chambers and of a formulation chamber for the final product (having a volume of the order of the milliliter), and
a part configured to receive at least one vial, preferably several vials, for example between 2 and 10 vials.

The internal architecture, which is fluidic, of the cassette is based on breaking down the radio-syntheses into successive steps.

As a matter of fact, to miniaturize a device for synthesizing a radioactive tracer, the usual steps of synthesis in terms of volume, flow and chemistry have had to be reorganized and adapted. Another difficulty has been to avoid the occurrence of bubbles. In other words, a difficulty in "miniaturizing" a device for synthesizing a radioactive tracer was in particular to avoid the occurrence of bubbles while making it possible to mix together different required reagents, this moreover being in capillaries and chambers which measure of the order of the micrometer.

Thus, although such a cassette constitutes an item of radioactive waste, in particular in the case of fluorine and gallium the radioactive impurities of which have a very long life, it enables minimization of the amounts of fluids used and thus a reduction in the waste generated and in the residual radioactivity after the synthesis, mainly due to its compactness.

The formulation chamber is mainly distinguished by its volume being greater than the other chambers.

In an example embodiment, the formulation chamber comprises a port, for example located in the upper part of the formulation chamber, which is configured to enable gas to be discharged at a step of filling the formulation chamber.

Furthermore, for example, it makes it possible to re-do a mixing step between a solution of NaCl and a radio-pharmaceutical substance.

In a favored embodiment, upstream of at least one reaction chamber is located at least one structure configured to mix at least two fluids, this being at least one mixing chamber.

For example, at least one mixing chamber is configured to mix a precursor, provided from a vial, to the radioisotope and/or to reduce the concentration of $CH_3CN$ (acetonitrile)

output from an HPLC column (HPLC being an initialism of "High Performance Liquid Chromatography") for example before a change in solvent.

For example, the precursor is stored in one of the vials. The precursor will react with the radioisotope to form a radioactive tracer, or even a radio-pharmaceutical injectable into an individual.

For example, the at least one mixing chamber comprises a capillary and the capillary comprises a wall at least part of which comprises a structure in relief.

Such a structure in relief, or microstructure, is thus configured to create turbulence, for example vortices, in fluid flows and thereby strongly increase mixing between the fluids.

A reaction chamber here is for example a cavity formed by widening of a section of a capillary.

In a favored example embodiment, the at least one reaction chamber is a chamber for reaction at temperature, that is to say for a reaction at a different temperature from the ambient temperature.

The chamber for reaction at temperature for example makes it possible to react the precursor with radioisotope, at different temperatures from the ambient temperature if required.

For example, the chamber for reaction at temperature is heated, that is to say that the temperature is brought to a higher temperature than the ambient temperature.

According to another example, it is also possible to cool the chamber for reaction at temperature, i.e. the temperature is brought to a lower temperature than the ambient temperature.

For example, it is cooled after a reaction to be able to transfer the liquid to the following steps, and/or for example to improve the yield of certain operations of chemistry (for example trapping molecules).

To that end, for example, a heating circuit comprises a heating/cooling element, that is to say an element configured to heat and cool, situated for example on a reception platform for the mounting card.

As a matter of fact, thanks to such a microfluidic cassette, that is to say a miniaturized device, it is thus possible to use a same element for heating or cooling a chamber; which is not possible for greater volumes.

In position, the chamber for reaction at temperature is thus in contact with the heating/cooling element for example.

In another favored example embodiment, the cassette comprises at least two reaction chambers one of which is a chamber for reaction at temperature and another is a reaction chamber then referred to as "conventional".

If the cassette comprises a chamber for reaction at temperature, the mounting card preferably further comprises a heat insulation flow route surrounding at least part of the chamber for reaction at temperature.

In an example embodiment, the heat insulation flow route comprises at least one recess passing through a thickness of the mounting card and extending around at least part of the chamber for reaction at temperature.

In other words, the chamber for reaction at temperature is preferably physically separated from the rest of the card, for example by virtue of an opening cut out in the card, thereby making it possible to avoid heating, or cooling, surrounding members by heat conduction.

Thus, the cassette can comprise a chamber for reaction at temperature even if it is not used, or is not used at temperature, in a method of synthesizing a radioactive tracer.

For example, for some radioactive tracer syntheses from carbon 11 in gaseous state, it is possible not to heat.

In an example embodiment, the card further comprises at least one vent upstream and/or at least one vent downstream of the chamber for reaction at temperature for discharging gases.

For example, a vent is controllable between an open position and a closed position.

According to another example, a vent comprises a porous membrane which enables gases to be discharged to the waste port, in particular when valves are open.

In a favored example embodiment, the at least one reaction chamber is loaded with beads, in other words it comprises a bead column.

In particular, this is preferably a conventional reaction chamber.

For example, according to the radioactive tracer to be synthesized, all the reaction chambers are loaded with beads: and preferably the conventional reaction chambers.

Preferably, a chamber for reaction at temperature has no beads.

Preferably, a chamber for reaction at temperature is empty before use of the cassette and is only filled by corresponding reagents and fluids during its use.

The beads are for example incorporated at the time of the manufacture of the card and are chosen according to needs, for example according to the desired synthesis and therefore according to the radioisotope, for a change in solvent, a pre-purification, a purification, etc.

Thus, the beads are possibly of different natures according to the reaction chamber in which they are included.

They are for example QMA beads (quaternary ammonium anion exchange), which promote anion capture, or alumina beads, which promote pre-purification of fluorinated radioactive tracers.

Preferably, the beads have a diameter of at least 25 μm (micrometers), or even of at least 30 μm.

In an advantageous example embodiment, the cassette further comprises a vial mounting. For example, the vial mounting is fastened, for example sealed, onto the mounting card. The vial mounting for example comprises at least one station configured to receive a vial where the at least one connector for supply by a vial enters.

Thus, in use for example, at least one vial is mounted on the vial mounting at a station and is connected to the at least one connector for supply by a vial of the microfluidic circuit.

Except for the radioisotope conveyed by the isotope port, all the reagents are provided by vials.

It is thus possible for the mounting card to contain no included reagent, except possibly for the beads.

The cassette is for example configured to comprise at least one vial, and preferably several vials, for example between 2 and 10 vials.

For example, among the stations configured to receive a vial, at least one station is configured to receive a vial of 4R type (for example ISO8362, a 4R vial, has a capacity of 6 mL (milliliter) but is generally filled to 4 mL maximum) and/or a station is configured to receive a vial of 15R type (a 15R vial has a capacity of 19 mL (milliliter) but is generally filled to 15 mL maximum).

The use and/or the station of the different vials are to be adapted according to the synthesis to be carried out. Nevertheless, some are frequently used, for example such as a vial of demineralized water ("DI water"), a vial of precursor, or for instance a vial of sodium chloride (NaCl).

Optionally, the cassette, or in particular the microfluidic circuit, further comprises at least one gas port configured to inject gas into the at least one vial.

Thus, the pressure of gas injected by the gas port, via a capillary, enables a fluid contained in the vial to be flushed via another capillary, that is to say by the connector for supply by a vial.

The capillary of the gas port thus opens from one side to a station configured to receive a vial of the vial mounting.

In an example embodiment, the cassette comprises at least one valve, preferably several valves, enabling the control of the fluids coming from the different interfaces, that is to say from the different vials and/or from the isotope port for example.

For example, the microfluidic circuit comprises at least one valve configured to open/close a capillary.

The cassette is for example possibly connected to a pneumatic line and a control command is configured to control the opening/closing of the at least one valve.

The at least one valve is individually controlled, that is to say that in case of a plurality of valves, each valve is controlled singly; for example by pneumatic or mechanical energy.

For example, each valve is controlled via a control command.

The at least one valve is actuated by a pressure comprised between approximately 0 and 7 bars but preferably around 3-4 bars.

They have very low dead volume and are activated/deactivated in less than one second. Such a valve also ensures an extremely low degree of leakage, even when it is used for the chamber for reaction at temperature; by way of example the chamber for reaction at temperature may undergo an internal pressure of a few bars on heating solvents to 130° C.

Such a valve is for example formed by a plastic membrane configured to close a capillary when a pressure is applied to it.

Thus, the number of valves actuated and/or the choice of vials, their number, their volume and their content, enable a certain flexibility in the sequencing of the reactions and of the synthesis steps.

According to another example, the cassette further comprises a fool-proof device configured to position the cassette.

In a particular example embodiment, such a fool-proof device is for example positioned to a side of the card, i.e. at a periphery of the card.

Such a fool-proof device here designates for example structures which enable a robot to grasp the cassette with precision to manipulate it in an automated space and/or different mechanical structures enabling the cassette to be positioned and/or aligned with an associated item of equipment. Such an environment comprising a robot and an associated item of equipment is for example described in application WO 2016/166486.

Furthermore, such a cassette is configured to be connected to:
  An HPLC column for a purification step which, on account of the technical and chemical requirements, is a step not easy to integrate into the microfluidic circuit, and still less for multiple syntheses; and/or
  A sterilizing filter, for a sterilizing filtration step: such a step is necessary to prepare the product to inject into an individual, this step, for legal and technical reasons, is easier to keep outside the cassette. An envisioned embodiment of the cassette however enables the integration of such a filter.

Thus, according to another example embodiment, the mounting card thus also comprises a sterilizing filter and a quality-control port serving to perform a test on exiting the sterilizing filter. For example, the sterilizing filter is positioned between the formulation chamber and the syringe port; the quality-control port is for example positioned in parallel with the syringe port, downstream of the sterilizing filter.

Favored modes of implementation mainly use three different radioisotopes, which are:
  $^{18}$F (fluorine 18) in solution in water enriched in $^{18}$O (oxygen 18), this solution for example being a cyclotron target,
  $^{11}$C (carbon 11), either in the form of gaseous iodomethane ($CH_3I$), propelled by helium (He), or liquid $CH_3I$ dissolved in DMSO (dimethylsulfoxide) or DMF (dimethylformamide), or gaseous $CH_3OTf$ (methyl triflate), or in the form of carbon monoxide CO, or in the form of carbon dioxide $CO_2$.
  $^{68}$Ga (gallium 68) in solution in water for example enriched in $^{68}$Zn (zinc 68), this solution being for example a cyclotron target; or a solution of $^{68}$Ga produced by a gallium 68 generator.

However, other radioisotopes may be used for example such as radioisotopes dedicated to unsealed source radiation therapy, for example such as 90-Yttrium, 177-Astate, 212-Lead or others.

Thus, such a cassette makes it possible to synthesize different radioactive tracers based on the same architecture. On exiting the cassette, it is possible to filter the radioactive tracer with a sterilizing filter in order to obtain a radiopharmaceutical product injectable into an individual.

According to another aspect, there is also provided a method for synthesizing a radioactive tracer in a cassette as described above comprising at least:
  a step of injecting into the microfluidic circuit a precursor via the at least one connector for supply by a vial and a radioisotope via the isotope port;
  a step of mixing the precursor and the radioisotope in at least one of the mixing chambers or reaction chambers;
  a step of synthesizing the radioactive tracer by reaction between the precursor and the radioisotope in at least one of the reaction chambers;
  a step of eluting the radioactive tracer by a solvent injectable into an individual in at least one of the reaction chambers;
  a step of diluting the radioactive tracer in a solution of NaCl in the formulation chamber; and
  a step of filling a syringe with NaCl solution comprising the radioactive tracer via the syringe port (SP).

For example, the solvent of the eluting step is for example ethanol or a solution of sodium dihydrogenphosphate.

In an example of implementation, the at least one reacting step comprises a step of reacting at temperature in the chamber for reaction at temperature.

In an example of implementation, the method further comprises a bubbling step in the formulation chamber to better mix a content of the formulation chamber.

Such a cassette in the same way as the associated method, for example has at least some of the following advantages:
  Limitation of the waste produced by the radio-pharmaceutical products,
  Limitation of the dead spaces and of the losses in the channels, in particular by virtue of the integrated valves and the smaller, shorter channels (the capillaries),
  Optimization of the volumes used of the reagents/beads/precursors, which reduces the corresponding costs,
  Total synthesis time reduced,
  Number of inlets/outlets greatly limited, thereby risk of leakage and in particular radioactive leakage limited,
  Improvement in the yields of the syntheses.

BRIEF DESCRIPTION OF THE DRAWINGS

The invention, according to an example embodiment, will be well understood and its advantages will be clearer on reading the following detailed description, given by way of illustrative example that is in no way limiting, with reference to the accompanying drawings in which.

DETAILED DESCRIPTION OF THE PREFERRED EMBODIMENTS

Identical parts represented in the aforementioned figures are identified by identical numerical references.

Figure 1:
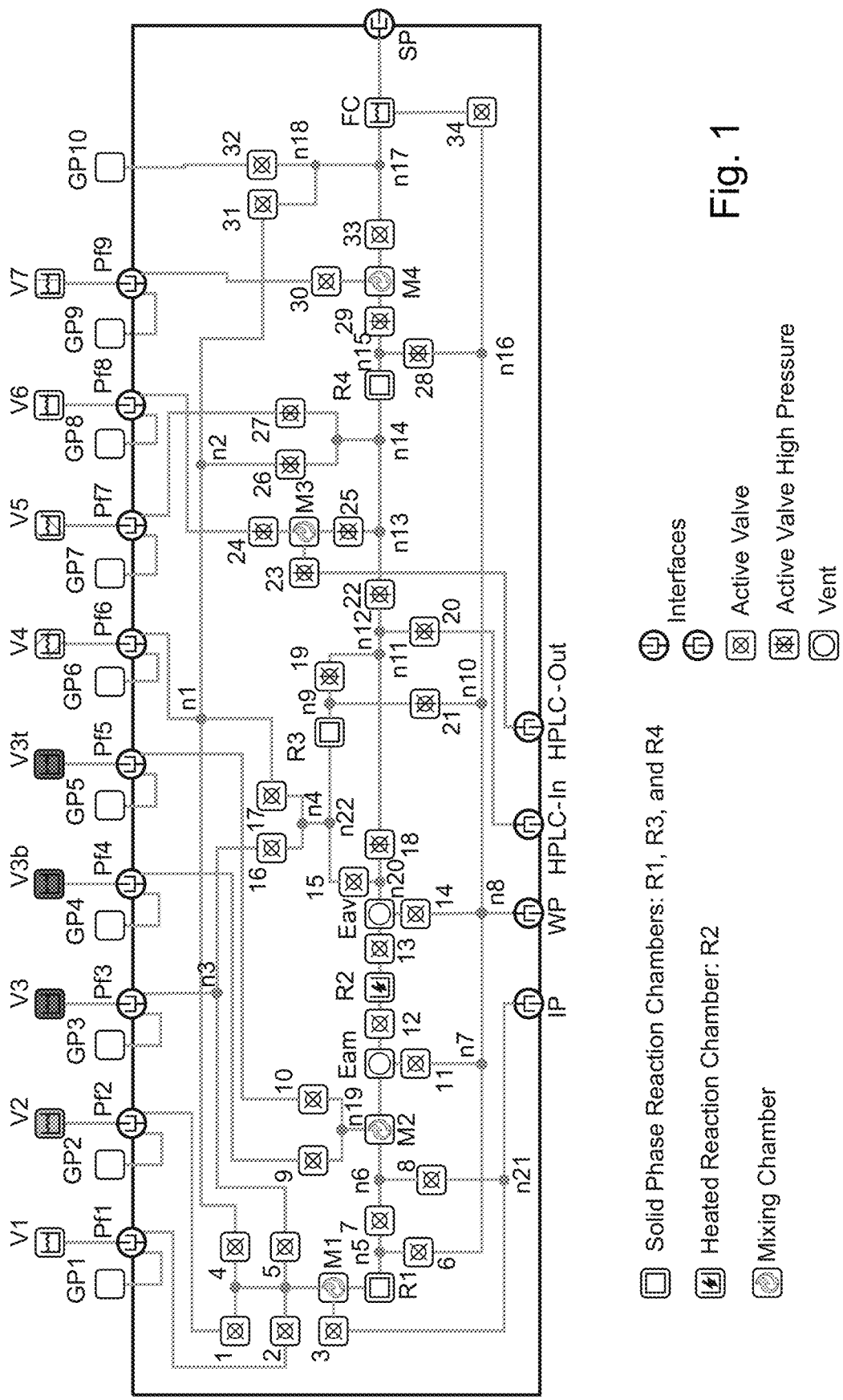
FIG. 1 shows an example of a functional architectural diagram of a cassette according to an example embodiment according to the invention.

FIG. 1 presents an example of a functional architectural diagram of a cassette according to an example embodiment of the invention.

Figure 2A:
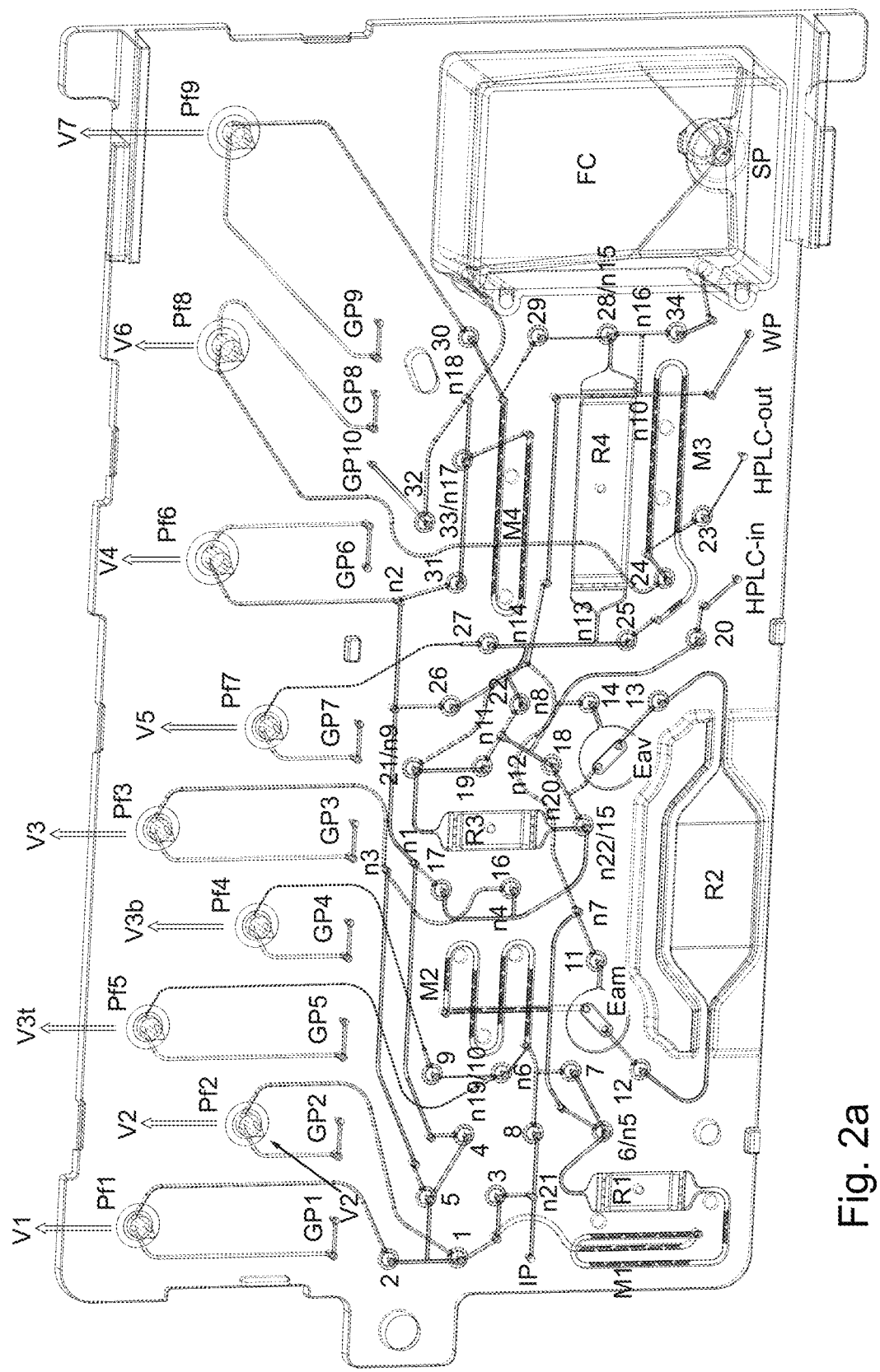
FIG. 2a presents a perspective view of a cassette according to an example embodiment.

Such a cassette comprises a mounting card, represented in FIG. 2a according to an example embodiment.

The mounting card measures for example 190 mm in length, 116 mm in width and 47 mm in height.

A mounting card of a cassette comprises a series of interfaces enabling inlets and outlets of fluids, that is to say liquids and/or gases, into or out from a microfluidic circuit.

Some of these interfaces are for example connectors for supply by a vial Pf, here schematically shown aligned at the top of the diagram.

A connector for supply by a vial is for example a hole formed in the mounting card to which is then connected at least one capillary.

The mounting card is connected here with 9 vials; the vials are here referenced V1, V2, V3, V3b, V3t, V4, V5, V6 and V7. The corresponding supply connectors are here referenced Pf1 to Pf9.

Among the vials, vials V1, V2, V3, V3b, V3t, V5 have a capacity of 6 mL and vials V4, V6, V7 have a capacity of 19 mL.

Another of these interfaces is for example a connector for connecting a syringe SP, also designating syringe port SP.

In the context of the present application, a syringe designates any container making it possible to collect the radioactive tracer obtained as output from the cassette; this designation includes for example here a reservoir or a bottle.

The syringe port SP is represented here to the right of the diagram.

The syringe port SP comprises for example a connector. This is for example a commercially-available connector of Tego® D-1000 type from Victus.

The syringe port SP also comprises for example a Luer port on which the connector is mounted.

And for example, this connector comprises a male part, to provide a fluid-tight connection which is normally closed, to which is then joined a sterilizing filter, itself connected to the syringe. In other words, the connector is placed between the Luer port and the sterilizing filter, via which may be connected the syringe.

Another of these interfaces is for example the isotope port IP which is configured to introduce a radioisotope into the microfluidic circuit.

Another of these interfaces is for example a waste port WP. Such a waste port in particular enables intermediate and/or surplus products to be extracted and/or disposed of as waste.

Others of these interfaces are inlet/outlet connectors into/from an HPLC column. Thus, the HPLC-in port enables an inlet into the HPLC column, thus an outlet from the cassette, and the HPLC-out port enables an outlet from the HPLC column, thus an inlet into the cassette after passing through the HPLC column. For this, rheodyne valves may be positioned between the HPLC-in and HPLC-out ports and the column.

In the present example embodiment, each port (HPLC in/out, isotope, waste) is merely formed here by a hole; the parts enabling a fluid-tight connection to be provided (seal or connector for example) are for example placed on the corresponding member to connect. Of course, each port could however comprise at least one fluid-tight join member, for example such as a seal Furthermore, the cassette comprises at least one gas port GP, here ten gas ports GP. The gas ports GP are referred here GP1 to GP10.

In an example embodiment not shown, at least one of the gas ports GP comprises a hydrophobic vent.

In the present example embodiment, the gas ports GP represent intakes for gas and are formed by a hole.

The gas ports referred GP1 to GP9 are each associated with supply connectors by a vial Pf.

Thus, these gas intakes are made in the different vials, referred Pf1 to Pf9, on use of the cassette. By injecting gas into the corresponding vial, the pressure of gas makes it possible to flush the fluid, or liquid, which it contains by a capillary separate from that by which the gas is injected.

In an example embodiment, the cassette may comprise for example a "spike" adjoining at least one of the connectors for supply by a vial; a spike is for example a connector of conical shape comprising at least two capillaries of which one communicates with the connector for supply by a vial and the other with the corresponding gas port and onto which is connected a vial on using the cassette.

The gas port GP10 is directly linked to a formulation chamber FC, described below, by a capillary and the gas port GP10 is configured to supply gas to that formulation chamber FC, in particular on filling a syringe, via the syringe port SP, to limit, or even to avoid, a depression.

In the present example embodiment, the microfluidic circuit comprises four reaction chambers R1, R2, R3, R4.

Here, the reaction chambers have the following capacities: R1 and R3: 50 µL, R2: 300 µL and R4: 200 µL.

The reaction chambers R1, R3 and R4 are conventional reaction chambers.

Furthermore, here they are loaded with beads.

For example, the reaction chamber R1 comprises beads QMA when it is used with fluorine 18 or gallium 68. For a synthesis based on carbon 11 it may be empty for example.

The beads here have a diameter of at most 30 µm.

The reaction chamber R2 is a chamber for reaction at temperature.

Thus, when the cassette is positioned in an installation, the chamber for reaction at temperature R2 is linked to a heating/cooling member for example.

The chamber R2 for reaction at temperature is preferably physically separate from the rest of the cassette, for example thanks to a cut-out in the card as illustrated in FIG. 2a so making it possible not to heat the structures around the chamber R2 for reaction at temperature by heat conduction.

The chamber R2 for reaction at temperature for example makes it possible to cause the reaction of a precursor, contained in one of the vials, for example the vial V3b or the vial V5, with the radioactive element introduced by the isotope port IP at temperatures that are different from the ambient temperature if necessary.

The microfluidic circuit also comprises mixing chambers M1 M2, M3, M4.

The mixing chambers M1 to M4 are for example capillaries with microstructures which create vortices in the fluid flows and thereby strongly increase the mixing between two fluids.

Figure 2B:
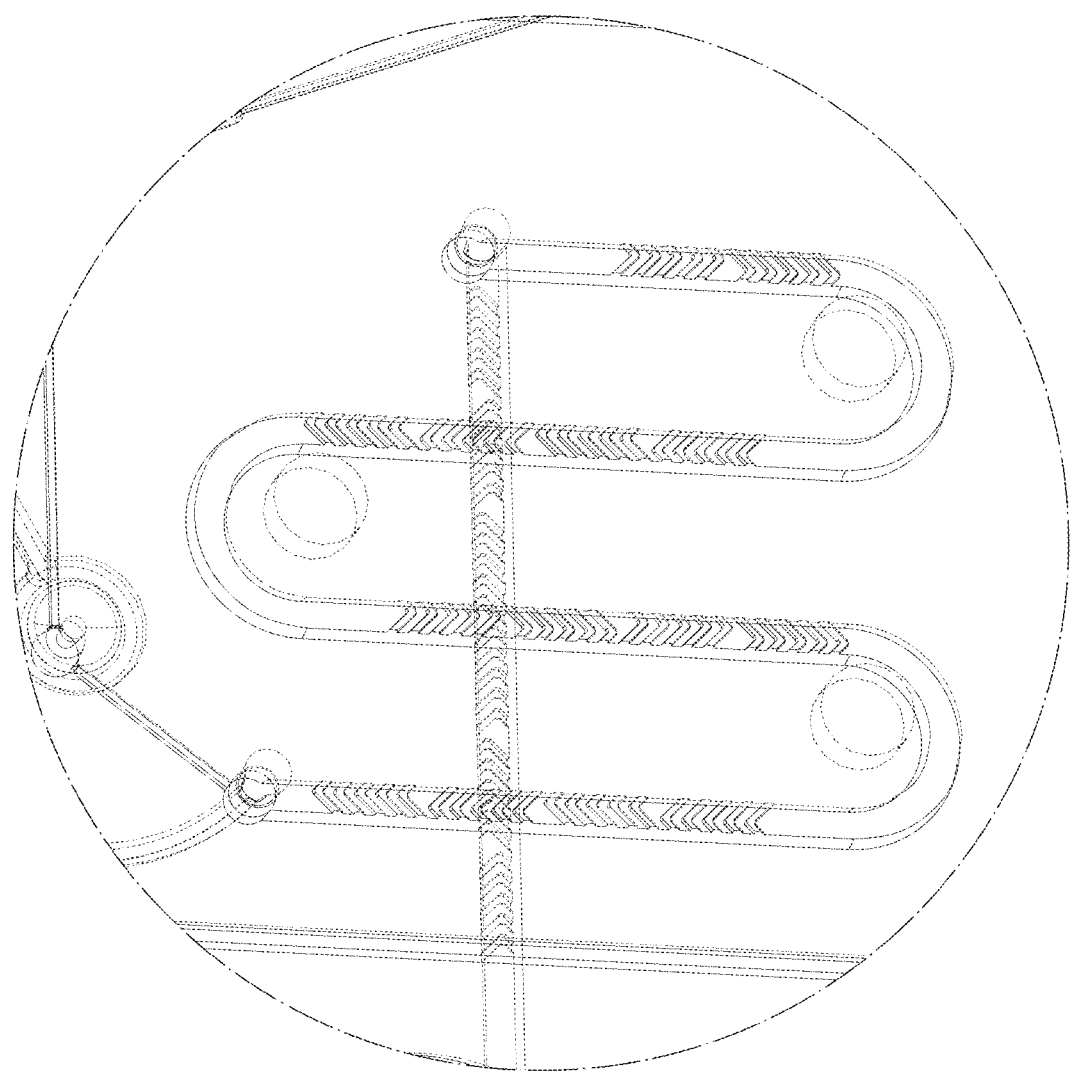
FIG. 2b shows an example embodiment of a mixing chamber, FIG. 3, comprising FIGS. 3.1 to 3.23, illustrates method steps for synthesizing a radioactive tracer from a radioisotope of fluorine 18 ($^{18}$F) according to an example of implementation of the invention, FIG. 4, comprising FIGS. 4.1 to 4.7, illustrates method steps for synthesizing a radioactive tracer from a radioisotope of carbon 11 ($^{11}$C) according to an example of implementation of the invention, and FIG. 5, comprising FIGS. 5.1 to 5.17, illustrates method steps for synthesizing a radioactive tracer from a radioisotope of gallium 68 ($^{68}$Ga) according to an example of implementation of the invention.

Such a mixing chamber is for example illustrated in FIG. 2b which is an enlargement of the mixing chamber M2.

Ahead, that is to say upstream of the reaction chambers R1, R2 and R4, are located the mixing chambers M1, M2 and M3. The mixing chamber M4 is downstream of the reaction chamber R4 and upstream of the formulation chamber FC.

The mixing chamber M2, positioned upstream of the chamber for reaction at temperature R2, in particular makes it possible to mix the precursor with the radioisotope.

The mixing chamber M3, positioned upstream of the reaction chamber R4 makes it possible for example to reduce a concentration of $CH_3CN$ on exiting HPLC before a change in solvent in the reaction chamber R4 and thereby to promote a change in solvent that provides good performance Lastly, the microfluidic circuit comprises the formulation chamber FC.

The formulation chamber for example has a capacity of the order of the milliliter, for example around ten milliliters, for example approximately 12 mL in the present example embodiment.

It is possibly provided with a port in its upper part to enable discharge of gas at the time it is filled for example.

The card diagrammatically illustrated in FIG. 1 comprises thirty-four valves enabling the control of the fluids coming from the various interfaces. The valves are numbered by 1 to 34. These valves for example are controlled singly by pneumatic energy via the command control. They are for example actuated at pressures of 0-7 bars but preferably around 3-4 bars.

Thus, the mounting card does not contain any included reagent, apart from the beads.

The reagents are all carried by the vials numbered by from V1 to V7 and the radioisotope arrives by the isotope port.

The use and station of the various vials is thus adaptable according to the synthesis which the radio-chemist wishes to perform.

Thus, in the present example of architecture, the mixing chamber M1 is linked by a capillary to the vial V1 (which capillary comprises the valve 2), by a capillary to the vial V2 (which capillary comprises the valve 1), by a capillary to the vial V3 (which capillary comprises the valve 5) and by a capillary to the vial V4 (which capillary comprises the valve 4).

Furthermore, the valve 1, the valve 2, the valve 4 and the valve 5 are linked together by capillaries.

The capillary between the valve 4 and the vial V4 comprises a node n1 to which is connected a capillary, comprising the valve 17, which connects to the reaction chamber R3, such that the mixing chamber M1 is furthermore linked to the reaction chamber R3 by a capillary (which comprises the valve 17).

The mixing chamber M1 is furthermore linked to the reaction chamber R4 by a capillary (which further comprises the valve 26) and to the formulation chamber FC by a capillary (which further comprises the valve 31).

A node n2 connects the capillary between the node n1 and the valve 31 to the capillary comprising the valve 26.

The capillary between the valve 5 and the vial V3 comprises a node n3 to which is connected a capillary, comprising the valve 16, which connects to the reaction chamber R3, such that the mixing chamber M1 is furthermore linked to the reaction chamber R3 by a capillary (which comprises the valve 16).

A node n4 on the capillary between the valve 16 and the reaction chamber R3 connects the capillary to the valve 17, and a node n22 between the reaction chamber R3 and the node n4 also enables a join by a capillary to the valve 15.

The mixing chamber M1 is also connected to the isotope port IP by a capillary which comprises the valve 3.

Lastly, the mixing chamber M1 is connected to the reaction chamber R1, upstream of the latter by a capillary.

The reaction chamber R1 is thus connected to the mixing chamber M1 and furthermore connected to the mixing chamber M2, to the isotope port, to the waste port and to the chamber for reaction at temperature by capillaries.

The capillary between the reaction chamber R1 and the mixing chamber M2 comprises the valve 7.

Between the reaction chamber R1 and the valve 7 a node n5 connects a capillary comprising the valve 6 and leading to the waste port WP.

Between the valve 7 and the mixing chamber M2 the capillary comprises a node n6 to which connect a capillary comprising the valve 8 and which connects to the capillary between the valve 3 and the isotope port IP at a node n21 to link the reaction chamber R1 to the isotope port IP.

The mixing chamber M2 is connected to the vial V3b by a capillary which comprises the valve 9 and to the vial V3t by a capillary which comprises the valve 10 which connects to the capillary between the mixing chamber M2 and the valve 9 at a node n19.

Between the mixing chamber M2 and the chamber for reaction at temperature R2, the capillary comprises a vent Eam and the valve 12 (which is between the vent and the chamber for reaction at temperature R2) which are thus considered to be upstream of the chamber for reaction at temperature R2.

Said upstream vent Eam is linked by a capillary comprising the valve 11 to the capillary between the valve 6 and the waste port WP at a node n7.

Between the valve 15 and the chamber for reaction at temperature R2, the capillary comprises a vent Eav and the valve 13 (which is between the vent and the chamber for reaction at temperature R2) which are thus considered to be downstream of the chamber for reaction at temperature R2.

Said downstream vent Eav is linked by a capillary comprising the valve 14 to the capillary between the node n7 and the waste port WP, at a node n8.

The reaction chamber R3 is thus linked to the valves 15, 16 and 17; and furthermore linked to the waste port WP, to the HPLC-in port, to the formulation chamber FC, to the mixing chamber M3 and to the reaction chamber R4.

The reaction chamber R3 is linked to the waste port WP by a capillary comprising the valve 21 connected at a node n10 to the capillary between the node n8 and the formulation chamber FC.

Between the reaction chamber R3 and the valve 21 the capillary comprises a node n9 to which connects a capillary, comprising the valve 19 and the valve 22, which connects to the reaction chamber R4.

Between the valves 19 and 22, a node n11 connects a capillary comprising the valve 18 to the capillary between the valve 15 and the vent downstream at a node n20.

Between the node 11 and the valve 22, a node n12 connects a capillary comprising the valve 20 to the HPLC-in port.

The mixing chamber M3 is linked to the vial V6 by a capillary which comprises the valve 24, to the HPLC-out port by a capillary which comprises the valve 23, and to the capillary between the valve 22 and the reaction chamber R4 at a node n13 by a capillary which here comprises the valve 25. Thus, the mixing chamber M3 is also linked at least to the HPLC-in port, or even also to the chamber for reaction at temperature R2, the reaction chamber R3 and to the vials V3 and V4 for example.

The reaction chamber R4 is connected to the vial V5 by a capillary comprising the valve 27.

A node n14 makes it possible to connect the capillaries between the valve 26 and the valve 27, to the capillary between the node n13 and the reaction chamber R4.

The reaction chamber R4 is also connected to the mixing chamber M4 by a capillary comprising the valve 29.

Between the reaction chamber R4 and the valve 29, a node n15 makes it possible to connect a capillary comprising the valve 28 to a capillary between the node n8 and the valve 34 at a node n16.

The mixing chamber M4 is considered downstream of the reaction chamber R4, linked thereto by a capillary comprising the valve 29, and upstream of the formulation chamber FC to which it is linked by a capillary comprising the valve 33.

The mixing chamber M4 is also at the same time linked to the formulation chamber FC by capillaries comprising the valve 29, 28 and 34.

In other words, the capillary between the formulation chamber FC and the node n16 comprises the valve 34.

The mixing chamber M4 is also linked to the vial V7 by a capillary comprising the valve 30.

Between the valve 33 and the formulation chamber FC, the capillary comprises a node n17 connecting a capillary comprising the valve 32 to the gas port GP10.

Between the valve 32 and the node n17, the capillary comprises a node n18 to which connects the capillary comprising the valve 31.

The valve 31 is thus between the node n2 and the node n18.

Lastly, the formulation chamber is at least connected to the mixing chamber M4 by the capillary comprising the valve 33, to the gas port GP10 by the capillary comprising the valve 32, to the vial V4 by the capillary comprising the valve 31 and to the waste port WP by the capillary comprising the valve 34. It is also connected to the syringe port SP by a capillary.

FIGS. 3, 4 and 5 make it possible to illustrate a use of such a cassette in a method of synthesizing radioactive tracer from different radioisotopes, in this case from fluorine 18, carbon 11 and gallium 68.

FIG. 3.1 illustrates the configuration of the cassette for a use with fluorine 18, for an aliphatic nucleophilic substitution.

Eight vials are used:
V1 filled with 4 mL of P2ET diluted in $CH_3CN$ (also denoted P2ET>$CH_3CN$)
V2 filled with 4 mL of $NaHCO_3$
V3 filled with 4 mL of $CH_3CN$
V3b filled with 4 mL of precursor
V4 filled with 15 mL of demineralized water ("DI water")
V5 filled with 4 mL of EtOH
V6 filled with 15 mL of demineralized water ("DI water")
V7 filled with 10 mL of NaCl The chambers used are:
R1 filled with QMA beads
R2 not containing any beads
R3 filed with $Al_2O_3$ beads (alumina)
R4 filled with C18 beads (silicon carbon)

The synthesis steps are next as follows:

Step 1 (FIG. 3.2): filling the reaction chamber R3 with demineralized water from the vial V4, and emptying by the waste port WP; opening of the valves 17 and 21;

Step 2 (FIG. 3.3): drying the reaction chamber R3 by gas via the isotope port IP, via the mixing chamber M2 and the chamber for reaction at temperature R2; opening the valves 8, 12, 13, 15 and 21; closing of the valve 17;

Step 3 (FIG. 3.4): filling the reaction chamber R3 with $CH_3CN$ contained in the vial V3; opening of the valve 16 and 21; closing of at least the valve 15;

Step 4 (FIG. 3.5): filling the reaction chamber R1, via the mixing chamber M1, with $NaHCO_3$ contained in the vial V2, and emptying by the waste port WP; opening of the valves 1 and 6; closing of the valves 16 and 21;

Step 5 (FIG. 3.6): filling the reaction chamber R1, via the mixing chamber M1, with demineralized water contained in the vial V4, and emptying by the waste port WP; opening of the valves 4 and 6; closing of the valve 1;

Step 6 (FIG. 3.7): filling the reaction chamber R4 with EtOH from the vial V5, and emptying by the waste port WP; opening of the valves 27 and 28; closing of the valves 4 and 6;

Step 7 (FIG. 3.8): filling the reaction chamber R4 with demineralized water from the vial V4, and emptying by the waste port WP; opening of the valves 26 and 28; closing of the valve 27;

Step 8: step carried out in the HPLC column, outside the card;

Step 9 (FIG. 3.9): injection of the $^{18}F$ isotope in anionic form in solution (in enriched water) by the isotope port IP into the reaction chamber R1, via the mixing chamber M1, trapping of at least some of the fluorine ions by the beads of the reaction chamber R1 and discharge of at least some of the enriched water by the waste port WP; opening of the valves 3 and 6; closing of the valve 26 and 28;

Step 10 (FIG. 3.10): drying of the reaction chamber R1, via the mixing chamber M1, by gas via the isotope port IP; opening, or keeping open, the valves 3 and 6;

Step 11 (FIG. 3.11): rinsing the reaction chamber R1, via the mixing chamber M1, with $CH_3CN$ from the vial V3, and discharge by the waste port WP; opening of the valves 5 and 6; closing of the valve 3;

Step 12 (FIG. 3.12): drying of the reaction chamber R1, via the mixing chamber M1, by vector gas via the isotope port IP; opening the valves 3 and 6; closing of the valve 5;

Step 13 (FIG. 3.13): injection of approximately 50 μL of P2ET>CH3CN from the vial V1 into the reaction chamber R1, via the mixing chamber M1, and discharge by the waste port WP; opening of the valves 2 and 6; closing of the valve 3;

Step 14 (FIG. 3.14): mixing of P2ET>CH3CN from the vial V1 with the precursor from the vial V3*b* into the mixing chamber M2, then reaction in the chamber for reaction at temperature R2; opening of the valves 2, 7, 9, 12 and 13, and of the valves 11 and 14; closing of the valve 6; discharge of bubbles via vents upstream and downstream of the chamber for reaction at temperature R2 if necessary;

Steps 15-17 (FIG. 3.15): heating of the chamber for reaction at temperature R2, establishing the reaction and cooling; closing of at least the valves 2, 7, 9, 11, 12, 13 and 14;

Step 18 (FIG. 3.16): propulsion to the HPLC column by the HPLC-in port, via the mixing chamber M2 and the reaction chamber R3, of the content of the chamber for reaction at temperature R2 by the gas introduced by the isotope port IP; opening of the valve 8, 12, 13, 15, 19 and 20;

Step 19-23: steps carried out in the HPLC column;

Step 24 (FIG. 3.17): after passing through the HPLC column, introduction of the purified radioactive tracer by the HPLC-out port, mixing with demineralized water from the vial V6 in the mixing chamber M3 and injection into the reaction chamber R4 then the liquid is discharged by the waste port WP; opening of the valves 23, 24, 25 and 28; closing of the valves 8, 12, 13, 15, 19 and 20;

Step 25 (FIG. 3.18): cleaning of the reaction chamber R4 with demineralized water from the vial V4 and evacuation by the waste port WP; the purified radioactive tracer being fixed to the beads of the reaction chamber R4; opening of the valves 26 and 28; closing of the valves 23, 24 and 25;

Steps 26-27 (FIG. 3.19): elution and change of solvent by EtOH from the vial V5, mixing with NaCl from the vial V7 in the mixing chamber M4, positioned downstream of the reaction chamber R4, and injection into the formulation chamber FC, discharge of a portion by the waste port WP; opening of the valves 27, 29, 30, 33 and 34; closing of the valves 26 and 28;

Step 28-29 (FIG. 3.20): filling of a syringe via the syringe port SP by the content of the formulation chamber FC, for this purpose injection of gas by the gas port GP10; opening of the valve 32; closing of the valve 27, 29, 30, 33 and 34; a filter is present outside the card; then filling of a syringe for a quality control in the same manner;

Step 30 (FIG. 3.21): drying of the filter positioned outside the card by the gas introduced by the port GP10;

Step 31 (FIG. 3.22): moistening of the filter by demineralized water from the vial V4; opening of the valve 31 and closing of the valve 32; and Step 32 (FIG. 3.23): conducting a bubble point test to check the integrity of the sterilizing filter; opening of the valve 32 and closing of the valve 31.

FIG. 4.1 illustrates the configuration of the cassette for a use with carbon 11 (for synthesis of 11C-methionine).

Four vials are used:
V4 filled with 15 mL of demineralized water ("DI water")
V5 filled with 4 mL of precursor
V6 filled with 15 ml of $NaH_2PO_4$
V7 filled with 10 ml of NaCl
The chambers used are:
R4 filled with C18+ beads (silicon carbon)
The synthesis steps are next as follows:
Step 1 (FIG. 4.2): filling the reaction chamber R4 with precursor from the vial V5, and discharge by the waste port WP; opening of the valves 27 and 28;

Step 2 (FIG. 4.3): bubbling by 11-$CH_3I$ injected by the isotope port IP of the reaction chamber R4, via the mixing chamber M2 and the chamber for reaction at temperature R2 and discharge by the waste port WP; opening of the valves 8, 12, 13, 18, 22 and 28; closing of the valve 27;

Steps 3 and 4 (FIG. 4.4): elution with $NaH_2PO_4$ of the vial V6 via the mixing chamber M3 and the reaction chamber R4 and mixing with NaCl from the vial V7 via the mixing chamber M4 in the formulation chamber FC; opening of the valves 24, 25, 29, 30, 33, 34; closing of the valves 8, 12, 13, 18, 22 and 28;

Step 5-7 (FIG. 4.5): filling of a syringe for a patient (the filter is outside the card) via the syringe port SP by the content of the formulation chamber FC, for that purpose injection of gas by the gas port GP10; opening of the valve 32; closing of the valves 24, 25, 29, 30, 33, 34; then filling of a syringe for a quality control in the same manner; then drying of the filter positioned outside the card by gas introduced by the port GP10;

Step 8 (FIG. 4.6): moistening of the filter by demineralized water from the vial V4; opening of the valve 31 and closing of the valve 32; and Step 9 (FIG. 4.7): conduction of a bubble point test; opening of the valve 32 and closing of the valve 31.

FIG. 5.1 illustrates the configuration of the cassette for a use with gallium 68 (68Ga-DOTANOC).

Eight vials are used:
V1 filled with 4 mL of NaCl
V2 filled with 4 mL of saline solution
V3*b* filled with 4 ml of precursor
V4 filled with 15 mL of demineralized water ("DI water")
V5 filled with 4 mL of EtOH
V6 filled with 15 mL of demineralized water ("DI water")
V7 filled with 10 mL of NaCl
The chambers used are:
R1 filled with QMA beads
R2 not containing any beads
R4 filled with C18 beads
The synthesis steps are next as follows:
Step 1 (FIG. 5.2): filling of the reaction chamber R1, via the mixing chamber M1, with NaCl 5M (at a concentration of 5 mol/L) from the vial V1, and emptying by the waste port WP; opening of the valves 2 and 6;

Step 2 (FIG. 5.3): drying of the reaction chamber R1, via the mixing chamber M1, by gas via the isotope port IP and discharge by the waste port WP; opening the valves 3 and 6; closing of the valve 2;

Step 3 (FIG. 5.4): filling the reaction chamber R4 with EtOH contained in the vial V5, and discharge by the waste port; opening of the valves 27 and 28; closing of the valves 3 and 6;

Step 4 (FIG. 5.5): filling the reaction chamber R4 with demineralized water contained in the vial V4, and emptying by the waste port WP; opening of the valves 26 and 28; closing of the valve 27;

Step 5: in the HPLC column;

Step 6 (FIG. 5.6): dilution of the $^{68}$Ga introduced by the isotope port IP in the saline solution from the vial V2 in the mixing chamber M1 and injection into the reaction chamber R1 then evacuation of at least some of the enriched water by the waste port WP, at least some of the 68Ga remaining fixed on the beads of the reaction chamber R1; opening of the valves 1, 3 and 6; closing of the valves 26 and 28;

Step 7 (FIG. 5.7): drying of the reaction chamber R1, via the mixing chamber M1, by vector gas via the isotope port IP; opening, or keeping open, the valves 3 and 6; closing of the valve 1;

Step 8-9 (FIG. 5.8): elution with demineralized water from the vial V4 in the reaction chamber R1, via the mixing chamber M1, with precursor from the vial V3b in the mixing chamber M2, then reaction in the chamber for reaction at temperature R2; opening of the valves 4, 7, 9, 12 and 13, and of the valves 11 and 14; closing of the valves 3 and 6; discharge of bubbles via vents upstream and downstream of the chamber for reaction at temperature R2 if necessary;

Sub-steps 10-12 (FIG. 5.9): heating of the chamber for reaction at temperature R2, establishing the reaction and cooling of the chamber for reaction at temperature R2; closing of the valves 4, 7, 9, 11, 12, 13 and 14;

Step 13 (FIG. 5.10): transfer of the content of the chamber for reaction at temperature R2 to the HPLC column by the HPLC-in port, by injection of gas by the isotope port IP, via the mixing chamber M2; opening of the valves 8, 12, 13, 18 and 20;

Step 14-17: in the HPLC column;

Step 18 (FIG. 5.11): after passing through the HPLC column, introduction of the purified radioactive tracer by the HPLC-out port, mixing with demineralized water from the vial V6 in the mixing chamber M3 and injection into the reaction chamber R4 then the liquid is discharged by the waste port WP; opening of the valves 23, 24, 25 and 28; closing of the valves 8, 12, 13, 18 and 20;

Step 19 (FIG. 5.12): cleaning of the reaction chamber R4 with demineralized water from the vial V4 and evacuation by the waste port WP, the radioactive tracer being fixed onto the beads of the reaction chamber R4; opening of the valves 26 and 28; closing of the valves 23, 24 and 25;

Steps 20-21 (FIG. 5.13): elution of the radioactive tracer by EtOH from the vial V5, mixing with NaCl from the vial V7 in the mixing chamber M4, positioned downstream of the reaction chamber R4, and injection into the formulation chamber FC, discharge of a portion by the waste port WP; opening of the valves 27, 29, 30, 33 and 34; closing of the valves 26 and 28;

Step 22-23 (FIG. 5.14): filling of a syringe for a patient via the syringe port SP by the content of the formulation chamber FC, for this purpose injection of gas by the gas port GP10; opening of the valve 32; closing of the valve 27, 29, 30, 33 and 34; a filter is present outside the card; and similarly for filling of a syringe for a quality control;

Step 24 (FIG. 5.15): drying of the filter positioned outside the card by the gas introduced by the port GP10;

Step 25 (FIG. 5.16): moistening of the filter by the demineralized water from the vial V4; opening of the valve 31 and closing of the valve 32; and Step 32 (FIG. 5.17): conduction of a bubble point test; opening of the valve 32 and closing of the valve 31.

The invention claimed is:

1. A microfluidic cassette for synthesizing a radioactive tracer comprising:
    A mounting card,
    A microfluidic circuit, at least partly integrated into the mounting card, comprising:
        at least one connector for supply by a vial (Pf), configured to connect a vial (V) to the microfluidic circuit,
        at least one isotope port (IP), configured for introducing a radioisotope into the microfluidic circuit,
        at least one reaction chamber (R1, R2, R3, R4), connected to the at least one connector for supply by a vial and to the at least one isotope port by capillaries,
        at least one mixing chamber (M1, M2, M3, M4), positioned upstream of the at least one reaction chamber (R1, R2, R3, R4) and connected to the at least one reaction chamber (R1, R2, R3, R4) upstream of which it is positioned by at least one capillary,
        at least one formulation chamber (FC), connected to the at least one isotope port (IP) and to the at least one connector for supply by a vial (Pf) and positioned downstream of the at least one reaction chamber (R1, R2, R3, R4), and
        at least one connector for connecting a syringe (SP), positioned downstream of the at least one formulation chamber (FC) and connected to the at least one formulation chamber by at least one capillary.

2. The cassette according to claim 1, wherein the at least one reaction chamber (R1, R3, R4) is loaded with beads.

3. The cassette according to claim 1, wherein the at least one reaction chamber is a chamber for reaction at temperature (R2), and the mounting card comprises a heat insulation flow route surrounding at least part of the chamber for reaction at temperature (R2).

4. The cassette according to claim 3, wherein the heat insulation flow route comprises at least one recess passing through a thickness of the mounting card and extending around at least part of the chamber for reaction at temperature (R2).

5. The cassette according to claim 3, wherein the microfluidic circuit comprises at least one vent (Eam) upstream and/or at least one vent downstream (Eav) of the chamber for reaction at temperature (R2) for discharging gases.

6. The cassette according to claim 1, wherein the at least one mixing chamber (M1, M2, M3, M4) comprises a capillary and the capillary comprises a wall at least part of which comprises a structure in relief.

7. The cassette according to claim 1, wherein the microfluidic circuit comprises at least one valve configured to open/close a capillary.

8. The cassette according to claim 1, further comprising a vial mounting on the mounting card, the vial mounting comprising at least one station configured to receive a vial where the at least one connector for supply by a vial enters.

9. A method for synthesizing a radioactive tracer in a cassette according to claim 1 comprising at least:
    a step of injecting into the microfluidic circuit a precursor via the at least one connector for supply by a vial (Pf) and a radioisotope via the isotope port (IP);
    a step of mixing the precursor and the radioisotope in at least one of the mixing chambers (M1, M2, M3, M4) or reaction chambers (R1, R2, R3, R4);
    a step of synthesizing the radioactive tracer by reaction between the precursor and the radioisotope in at least one of the reaction chambers (R1, R2, R3, R4);
    a step of eluting the radioactive tracer by a solvent injectable into an individual in at least one of the reaction chambers (R1, R3, R4);
    a step of diluting the radioactive tracer in a solution of NaCl in the formulation chamber (FC); and
    a step of filling a syringe with NaCl solution comprising the radioactive tracer via the syringe port (SP).

10. The method according to claim 9, wherein the at least one reacting step comprises a step of reacting at temperature in the chamber for reaction at temperature (R2).

11. The cassette according to claim 4, wherein the microfluidic circuit comprises at least one vent (Eam) upstream and/or at least one vent downstream (Eav) of the chamber for reaction at temperature (R2) for discharging gases.

12. The cassette according to claim 2, wherein the at least one mixing chamber (M1, M2, M3, M4) comprises a capillary and the capillary comprises a wall at least part of which comprises a structure in relief.

13. The cassette according to claim 3, wherein the at least one mixing chamber (M1, M2, M3, M4) comprises a capillary and the capillary comprises a wall at least part of which comprises a structure in relief.

14. The cassette according to claim 4, wherein the at least one mixing chamber (M1, M2, M3, M4) comprises a capillary and the capillary comprises a wall at least part of which comprises a structure in relief.

15. The cassette according to claim 5, wherein the at least one mixing chamber (M1, M2, M3, M4) comprises a capillary and the capillary comprises a wall at least part of which comprises a structure in relief.

16. The cassette according to claim 2, wherein the microfluidic circuit comprises at least one valve configured to open/close a capillary.

17. The cassette according to claim 3, wherein the microfluidic circuit comprises at least one valve configured to open/close a capillary.

18. The cassette according to claim 4, wherein the microfluidic circuit comprises at least one valve configured to open/close a capillary.

19. The cassette according to claim 5, wherein the microfluidic circuit comprises at least one valve configured to open/close a capillary.

20. The cassette according to claim 6, wherein the microfluidic circuit comprises at least one valve configured to open/close a capillary.

\* \* \* \* \*